(12) United States Patent
Cheng

(10) Patent No.: US 12,325,221 B2
(45) Date of Patent: Jun. 10, 2025

(54) ELASTIC COMPOSITE NON-WOVEN FABRIC AND MANUFACTURING EQUIPMENT AND MANUFACTURING METHOD OF THE SAME

(71) Applicant: GOLDEN PHOENIX FIBERWEBS, INC., Tainan (TW)

(72) Inventor: Kenneth Cheng, Taipei (TW)

(73) Assignee: GOLDEN PHOENIX FIBERWEBS, INC., Tainan (TW)

( * ) Notice: Subject to any disclaimer, the term of this patent is extended or adjusted under 35 U.S.C. 154(b) by 288 days.

(21) Appl. No.: 17/980,110

(22) Filed: Nov. 3, 2022

(65) Prior Publication Data

US 2024/0075704 A1    Mar. 7, 2024

(30) Foreign Application Priority Data

Sep. 2, 2022    (TW) .................................. 111133301

(51) Int. Cl.
| | |
|---|---|
| B29C 65/00 | (2006.01) |
| B32B 5/02 | (2006.01) |
| B32B 5/26 | (2006.01) |
| B32B 27/12 | (2006.01) |
| B32B 27/32 | (2006.01) |
| B32B 37/00 | (2006.01) |

(Continued)

(52) U.S. Cl.
CPC .............. *B32B 5/266* (2021.05); *B32B 5/022* (2013.01); *B32B 27/12* (2013.01); *B32B 27/32* (2013.01); *B32B 37/0053* (2013.01); *B32B 37/10* (2013.01); *B32B 37/1284* (2013.01); *B29C 66/1122* (2013.01); *B29C 66/433* (2013.01); *B29C 66/7294* (2013.01); *B29C 66/81435* (2013.01); *B29C 66/83413* (2013.01); *B32B 2262/0253* (2013.01); *B32B 2307/51* (2013.01); *B32B 2323/04* (2013.01); *B32B 2323/10* (2013.01); *B32B 2325/00* (2013.01)

(58) Field of Classification Search
CPC ........ B29C 66/83413; B29C 66/81435; B29C 66/433; B29C 66/7294; B29C 66/1122
See application file for complete search history.

(56) References Cited

U.S. PATENT DOCUMENTS

| | | |
|---|---|---|
| 5,244,482 A | 9/1993 | Hassenboehler, Jr. et al. |
| 5,527,416 A * | 6/1996 | Traise .................. B31F 5/04 156/290 |

(Continued)

*Primary Examiner* — Seyed Masoud Malekzadeh
(74) *Attorney, Agent, or Firm* — RABIN & BERDO, P.C.

(57) ABSTRACT

Provided are an elastic composite non-woven fabric and a manufacturing equipment and a manufacturing method thereof, wherein the elastic composite non-woven fabric manufacturing equipment includes an upper feed roller, an upper shrink roller, an upper bonding roller, upper fins, an middle feed roller, an winding roller, a lower feed roller, a lower shrink roller, a lower bonding roller, and lower fins. Wherein, two elastic non-woven fabrics shrink inward by the shrink roller and enter the gaps among the fins and grooves and teeth of the bonding roller to form regular wavy folds; the two pre-shrunk elastic non-woven fabrics are bonded to the upper and lower surfaces of the elastic material in a flat state by the aligned and adjacently disposed teeth of the bonding roller, thereby forming an elastic composite non-woven fabric.

5 Claims, 13 Drawing Sheets

(51) Int. Cl.
*B32B 37/10* (2006.01)
*B32B 37/12* (2006.01)

(56) References Cited

U.S. PATENT DOCUMENTS

| | | | | |
|---|---|---|---|---|
| 2005/0095405 A1* | 5/2005 | Park | ............... | B29C 66/80 |
| | | | | 425/363 |
| 2009/0191779 A1* | 7/2009 | Cree | ............... | B29C 66/21 |
| | | | | 442/361 |
| 2012/0033900 A1* | 2/2012 | Fraser | ............... | B29C 66/81435 |
| | | | | 156/227 |
| 2012/0063706 A1* | 3/2012 | Fraser | ............... | B29C 66/81435 |
| | | | | 493/243 |
| 2012/0096688 A1* | 4/2012 | Cheng | ............... | B29C 66/81435 |
| | | | | 24/442 |
| 2012/0251771 A1* | 10/2012 | Wilson | ............... | B29C 66/83413 |
| | | | | 428/137 |
| 2015/0036951 A1* | 2/2015 | Fraser | ............... | B32B 27/08 |
| | | | | 383/105 |
| 2015/0071574 A1* | 3/2015 | Fraser | ............... | B29C 66/8511 |
| | | | | 383/109 |
| 2017/0008261 A1* | 1/2017 | Jean-Mary | ............... | B32B 27/08 |
| 2018/0194099 A1* | 7/2018 | Wilcoxen | ............... | B29C 66/83511 |
| 2018/0244433 A1* | 8/2018 | Borchardt | ............... | B29C 66/73921 |
| 2018/0333943 A1* | 11/2018 | Middlesworth | ............... | B32B 5/26 |
| 2020/0368995 A1* | 11/2020 | Wilcoxen | ............... | B29C 66/73921 |

* cited by examiner

ELASTIC COMPOSITE NON-WOVEN FABRIC AND MANUFACTURING EQUIPMENT AND MANUFACTURING METHOD OF THE SAME

CROSS-REFERENCE TO RELATED APPLICATION

This application claims the priority of Taiwanese patent application No. 111133301, filed on Sep. 2, 2022, which is incorporated herewith by reference.

BACKGROUND OF THE INVENTION

1. Field of the Invention

The present invention relates to an elastic composite non-woven fabric and a manufacturing equipment and a manufacturing method thereof, and more particularly, to an elastic composite non-woven fabric, which is formed by bonding pre-shrunk elastic non-woven fabrics and an elastic material, and the manufacturing equipment and manufacturing method thereof.

2. The Prior Arts

Generally, when considering hygiene and using safety, sanitary products, such as masks, disposable clothing, baby diapers or adult diapers, or sport protective bandages, medical bandages, etc. are usually provided in one-time or disposable forms to avoid contamination by germs or harmful substances. Since these products will be in contact with a user's skin for a period of time, the air breathability requirements thereof are stricter to prevent discomfort or allergy, itching, and even rash of the skin caused by stuffiness or moisture.

Because the non-woven fabrics made of plastic materials have the advantages of being easy to manufacture and process, good chemical resistance, durability and low cost, they have been widely used in many sanitary products. However, the non-woven fabrics have poor extensibility and insufficient comfort and wrapping performance, which may cause inconvenience in wearable applications, such as diapers. Therefore, a composite type of non-woven fabrics called elastic composite non-woven fabrics, which can improve the extensibility, have been developed in this industry.

In the manufacturing process of existing elastic composite non-woven fabrics, a common method is to stretch a piece of elastic material in advance as a middle layer, and then use two pieces of ordinary inelastic non-woven fabrics respectively as upper and lower layers to perform bonding in a sandwich manner, and stop applying the external force used for stretching after bonding. At this time, the elastic material recovers to its natural state due to tensile property, and the ordinary non-woven fabrics bonded to the upper and lower surfaces of the elastic material are formed with wavy folds. In this method, the elastic composite non-woven fabric is produced in a manner without damaging the non-woven fabric structure.

Another common method is to use a piece of elastic material in non-stretched state as a middle layer, and then use two pieces of ordinary inelastic non-woven fabrics respectively as upper and lower layers to perform bonding in a sandwich manner, thereby forming a flat three-layer structure. After bonding, the ordinary non-woven fabric material is imparted with slight extensibility by destroying the surface of the ordinary non-woven material, such as activation, without damaging the elastic material. In this method, the non-woven fabrics are damaged during the activation process, thereby its tensile strength is insufficient and it is prone to be torn.

Further, in the prior art, the extensibility of elastic composite non-woven fabrics is a popular requirement. However, in the prior art, the improvement for the requirement of recovery ability of elastic composite non-woven fabrics (especially elastic materials) is rare.

However, since the ordinary inelastic non-woven fabrics have almost no extensibility, it will reach the tensile limit after being slightly stretched, and thus is prone to be torn; in addition, the cross-direction tensile limit of such elastic composite non-woven fabrics is equal to that of ordinary inelastic non-woven fabrics. Thereby, the existing elastic composite non-woven fabrics have the following several problems: first, there are limitations in stretching, as the tensile limit of the elastic composite non-woven fabrics is mostly limited by the tensile limit of non-woven fabric materials; second, the tensile strength is insufficient and they are prone to be torn, as the structures of the non-woven fabric and the elastic material are prone to be damaged during the activation, resulting in insufficient tensile strength; third, the material is not breathable; fourth, the extensibility and recovery force are insufficient and the production efficiency is low, therefore, the stretching is necessary to be carried out on an elastic material with larger area for satisfying its requirements for stretching and recovery force.

SUMMARY OF THE INVENTION

A primary objective of the present invention is to provide an elastic composite non-woven fabric, which is formed by bonding pre-shrunk elastic non-woven fabrics and an elastic material together. By the manufacturing equipment or manufacturing method of the elastic composite non-woven fabric according to the present invention, the elastic non-woven fabrics with high elongation, high tensile strength and high recovery force are bonded to the elastic material after being wavy inwardly arranged to form the elastic composite non-woven fabric, so that the surface of the formed elastic composite non-woven fabric will be formed with a certain degree of adjustable, regular wavy folds.

Another objective of the present invention is to provide an elastic composite non-woven fabric in which the more the elastic material extends, the greater its recovery force, thus it is possible to use the shorter cutting widths to meet higher extension and recovery requirements.

As used herein, "natural width" refers to the width of a material in a state of being not shrunk or stretched by an external force.

As used herein, "elongation" refers to the ratio of the stretching amount with respect to the natural width of a material to the natural width.

As used herein, "shrinkage" refers to the ratio of the shrinking amount with respect to the natural width, of the elastic non-woven fabric after being wavy inwardly arranged, to the natural width.

As used herein, "recovery force" refers to the tensile force that a material is subjected when being stretched.

As described herein, "stretching", "shrinking/contracting" and "heat contraction" are all carried out in the cross direction, unless otherwise indicated.

In order to achieve the foregoing objectives, the present invention provides a manufacturing equipment for an elastic composite non-woven fabric, comprising:

an upper part, which is provided with an upper feed roller, an upper shrink roller, an upper bonding roller, and a plurality of upper fins;

a middle part, which is provided with a middle feed roller and a winding roller; and a lower part, which is provided with a lower feed roller, a lower shrink roller, a lower bonding roller, and a plurality of lower fins, wherein the upper shrink roller and the lower shrink roller each includes:

a body, which is in a column shape;

a first thread and a second thread, which are disposed on the body of corresponding one of the upper shrink roller and the lower shrink roller, and arranged symmetrically with respect to a mid-perpendicular plane of a longitudinal axis of the corresponding one of the upper shrink roller and the lower shrink roller; and the upper bonding roller and the lower bonding roller each includes:

a main body, which is in a column shape;

a plurality of teeth, which are provided, in parallel to each other at a fixed interval, on an outer peripheral surface of the main body of corresponding one of the upper bonding roller and the lower bonding roller, and perpendicular to a longitudinal axis of the corresponding one of the upper bonding roller and the lower bonding roller; and a plurality of grooves, which are formed in a portion of the corresponding one of the upper bonding roller and the lower bonding roller where the teeth are not disposed; and the upper fins and the lower fins are each in a flat shape and each includes:

a first end pivotally fixed to the manufacturing equipment for the elastic composite non-woven fabric;

a second end disposed in a corresponding one of the grooves; and a shoulder disposed between the first end and the second end;

wherein a contour of each of the upper fins and the lower fins from the shoulder to the second end substantially matches a contour of the outer peripheral surface of the main body of corresponding one of the upper bonding roller and the lower bonding roller; and wherein the upper feed roller, the middle feed roller, and the lower feed roller respectively feed a first elastic non-woven fabric, an elastic material, and a second elastic non-woven fabric, the upper shrink roller receives the first elastic non-woven fabric, and the first thread and the second thread of the upper shrink roller are symmetrically arranged such that the first elastic non-woven fabric shrinks toward a center thereof along a direction parallel to the upper shrink roller, thereby the first elastic non-woven fabric enters gaps among the upper fins and the grooves and the teeth of the upper bonding roller in a non-stretched state, so that the first elastic non-woven fabric is wavy inwardly arranged and formed with regular wavy folds, the lower shrink roller receives the second elastic non-woven fabric, and the first thread and the second thread of the lower shrink roller are symmetrically arranged such that the second elastic non-woven fabric shrinks toward a center thereof along a direction parallel to the lower shrink roller, thereby the second elastic non-woven fabric enters gaps among the lower fins and the grooves and the teeth of the lower bonding roller in a non-stretched state, so that the second elastic non-woven fabric is wavy inwardly arranged and formed with regular wavy folds, wherein a rotational speed of the upper feed roller, the upper shrink roller, the lower feed roller and the lower shrink roller is greater than that of the upper bonding roller and the lower bonding roller, thereby resulting a speed difference, and the first elastic non-woven fabric and the second elastic non-woven fabric are introduced between the upper fins and the lower fins due to the speed difference;

the teeth of the upper bonding roller and the teeth of the lower bonding roller are aligned and adjacently disposed, respectively, such that the first elastic non-woven fabric pre-shrunk and formed with the regular wavy folds, the elastic material fed by the middle feed roller, and the second elastic non-woven fabric pre-shrunk and formed with the regular wavy folds are bonded together at a portion where the teeth of the upper bonding roller and the teeth of the lower bonding roller are contacted, thereby forming the elastic composite non-woven fabric, and the winding roller winds the elastic composite non-woven fabric for collection.

In order to achieve the foregoing objectives, the present invention further provides an elastic composite non-woven fabric, comprising:

an elastic material, which is in a planar shape, and includes an elastic film, an elastomeric non-woven fabric, or a combination thereof, and a first elastic non-woven fabric and a second elastic non-woven fabric, which are wavy inwardly arranged and formed with regular wavy folds, wherein the first elastic non-woven fabric and the second elastic non-woven fabric are respectively bonded to an upper surface and a lower surface of the elastic material in a manner that the first elastic non-woven fabric and the second elastic non-woven fabric each are pre-shrunk and formed with the regular wavy folds, wherein the wavy folds of the first elastic non-woven fabric and the second elastic non-woven fabric are aligned and symmetrical to each other relative to the elastic material, wherein the first elastic non-woven fabric and the second elastic non-woven fabric each have an elongation of 50 to 200%, the first elastic non-woven fabric and the second elastic non-woven fabric each have a shrinkage of 50 to 85%, the elastic material has an elongation of 600 to 1300%, and the elastic composite non-woven fabric has an elongation of 300 to 1000%.

In order to achieve the foregoing objectives, the present invention further provides a manufacturing method of an elastic composite non-woven fabric, comprising:

a feeding step, feeding a first elastic non-woven fabric, an elastic material, and a second elastic non-woven fabric, respectively, wherein the first elastic non-woven fabric and the second elastic non-woven fabric each have an elongation of 50 to 200%, and the elastic material includes an elastic film, an elastomeric non-woven fabric, or a combination thereof, a first shrinking step wherein the first elastic non-woven fabric is wavy inwardly arranged and formed with regular wavy folds by an upper shrink roller, an upper bonding roller, and a plurality of upper fins, wherein the upper shrink roller includes:
  a body, which is in a column shape;
  a first thread and a second thread, which are disposed on the body of the upper shrink roller, and arranged symmetrically with respect to a mid-perpendicular plane of a longitudinal axis of the upper shrink roller; and
the upper bonding roller includes:
  a main body, which is in a column shape;
  a plurality of teeth, which are provided, in parallel to each other at a fixed interval, on an outer peripheral surface of the upper bonding roller, and perpendicular to a longitudinal axis of the upper bonding roller; and
  a plurality of grooves, which are formed in a portion of the upper bonding roller where the teeth are not disposed; and
the upper fins are each in a flat shape and each includes:
  a first end for pivotally fixing corresponding one of the upper fins;
  a second end disposed in a corresponding one of the grooves; and
  a shoulder disposed between the first end and the second end of the corresponding one of the upper fins;
wherein, in the first shrinking step, the first elastic non-woven fabric shrinks toward a center thereof along a direction parallel to the upper shrink roller by the first thread and the second thread of the upper shrink roller which are symmetrically arranged, thereby the first elastic non-woven fabric enters gaps among the upper fins and the grooves and the teeth of the upper bonding roller in a non-stretched state, and is formed with the regular wavy folds;
a second shrinking step wherein the second elastic non-woven fabric is wavy inwardly arranged and formed with regular wavy folds by a lower shrink roller, a lower bonding roller, and a plurality of lower fins, wherein
the lower shrink roller includes:
  a body, which is in a column shape;
  a first thread and a second thread, which are disposed on the body of the lower shrink roller, and arranged symmetrically with respect to a mid-perpendicular plane of a longitudinal axis of the lower shrink roller; and
the lower bonding roller includes:
  a main body, which is in a column shape;
  a plurality of teeth, which are provided, in parallel to each other at a fixed interval, on an outer peripheral surface of the lower bonding roller, and perpendicular to a longitudinal axis of the lower bonding roller; and
  a plurality of grooves, which are formed in a portion of the lower bonding roller where the teeth are not disposed; and
the lower fins are each in a flat shape and each includes:
  a first end for pivotally fixing corresponding one of the lower fins;
  a second end disposed in a corresponding one of the grooves; and
  a shoulder disposed between the first end and the second end of the corresponding one of the lower fins; and
wherein, in the second shrinking step, the second elastic non-woven fabric shrinks toward a center thereof along a direction parallel to the lower shrink roller by the first thread and the second thread of the lower shrink roller which are symmetrically arranged, thereby the second elastic non-woven fabric enters gaps among the lower fins and the grooves and the teeth of the lower bonding roller in a non-stretched state, and is formed with the regular wavy folds;
a bonding step, bonding the first elastic non-woven fabric, the elastic material, and the second elastic non-woven fabric together, wherein the teeth of the upper bonding roller and the teeth of the lower bonding roller are aligned and adjacently disposed, respectively, such that the first elastic non-woven fabric pre-shrunk by the first shrinking step, the fed elastic material, and the second elastic non-woven fabric pre-shrunk by the second shrinking step are pressed and bonded together at a portion where the teeth of the upper bonding roller and the teeth of the lower bonding roller are contacted, thereby forming the elastic composite non-woven fabric;
wherein a rotational speed of the upper feeding roller and the lower feeding roller in the feeding step, a rotational speed of the upper shrink roller in the first shrinking step, and a rotational speed of the lower shrink roller in the second shrinking step are greater than the that of the upper bonding roller and the lower bonding roller in the bonding step, thereby resulting a speed difference, and the first elastic non-woven fabric and the second elastic non-woven fabric are introduced between the upper fins and the lower fins due to the speed difference;
wherein the first elastic non-woven fabric after the first shrinking step and the second elastic non-woven fabric after the second shrinking step each have a shrinkage of 50 to 85%.

The effectiveness of the present invention is that, for example, by means of the manufacturing equipment or manufacturing method of the elastic composite non-woven fabric, the two pieces of elastic non-woven fabrics are pre-shrunk to form wavy surfaces first, and then the two pieces of pre-shrunk elastic non-woven fabrics are bonded to the upper surface and the lower surface of the elastic material, respectively. Therefore, the elastic composite non-woven fabric of the present invention can have high elongation, high tensile strength and high recovery force, so that the surface of the elastic composite non-woven fabric will be formed with a certain degree of regular wavy folds.

In addition, because the elongation of the elastic composite non-woven fabric is greatly improved, the user can use a smaller cutting width. Therefore, in the factory, it is possible to divide each cylindrical master-roll of the elastic composite non-woven fabric into more cylindrical sub-rolls of the elastic composite non-woven fabric, thereby improving the production efficiency.

Referring to FIG. 1, which shows the results of tensile test for the elastic material of the present invention with different cutting widths, wherein the width of the small cut piece is 5 cm, and the width of the large cut piece is 10 cm. The conditions and method for tensile test are the same as those described below for Examples 1 to 6, except that the method for tensile test is to stretch the elastic material from its natural state to the tensile limit, that is, until it is broken. As can be seen from FIG. 1, for the large cut piece, an elongation of 791% (that is, stretched to a width of 8.91 times the natural width thereof) is required to achieve a recovery force of 3000 g/in; while for the small cut piece, only an elongation of 422% (that is, stretched to a width of 5.22 times the natural width thereof) is required to achieve the same recovery force. In addition, the elongation of the large cut piece of elastic material (900 to 950%) is approximately twice that of the small cut piece of elastic material (approximately 450%) when the tensile limit (the end of the curves) is reached.

Moreover, the elastic composite non-woven fabric of the present invention can meet the requirements of higher stretchability and recovery force with smaller cutting width, which can greatly improve the comfort and wrapping performance.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
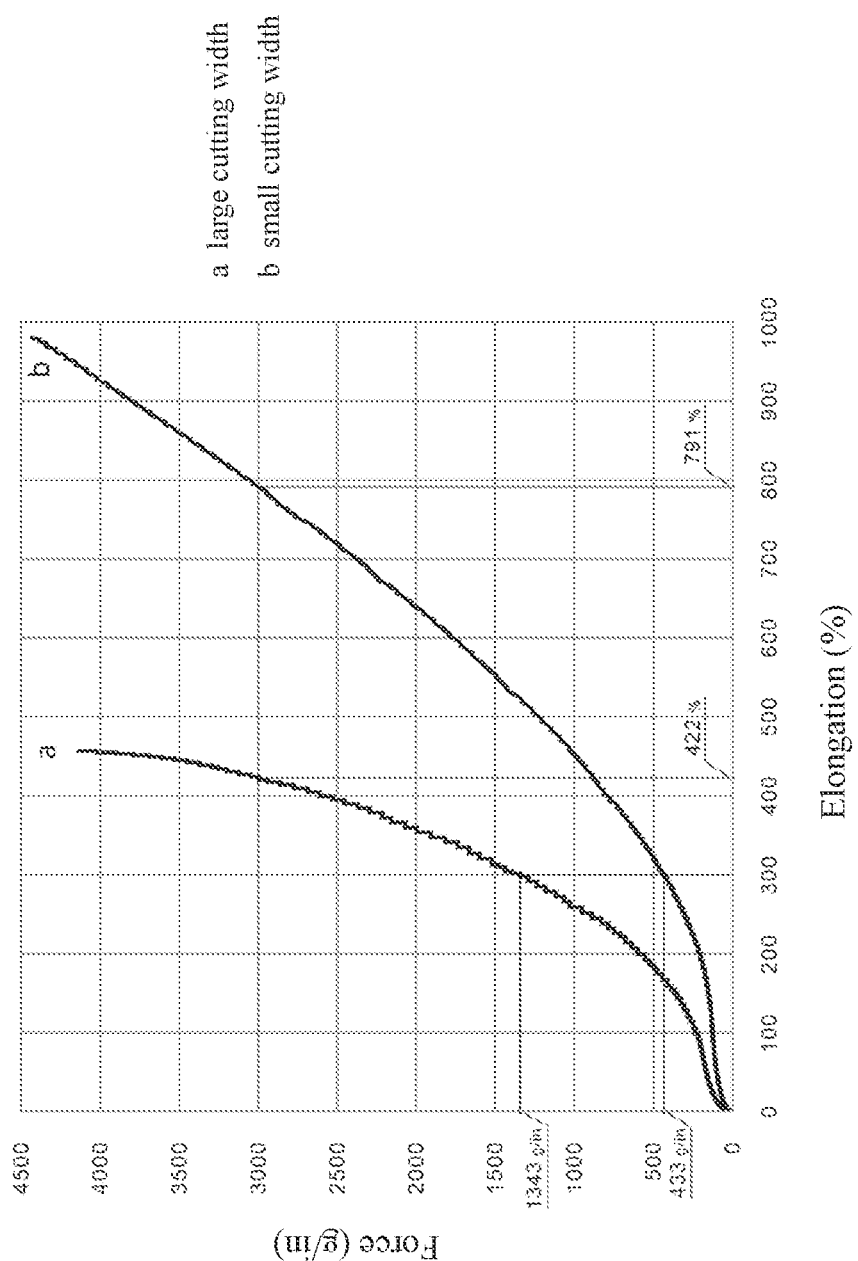
FIG. 1 illustrates the results of tensile test for the elastic material of the present invention with different cutting widths.

Embodiments of the present invention will be described in more detail below with reference to the drawings and the reference numerals, such that those skilled in the art can implement it after studying this description.

In this description, a natural width is defined as a width in a natural state without being stretched or shrunk by an external force.

In the present specification, all of the technical features of any one of the elastic composite non-woven fabric, the manufacturing equipment thereof, and the manufacturing method thereof according to the present invention can be applied to any one of the elastic composite non-woven fabric, the manufacturing equipment thereof, and the manufacturing method thereof according to the present invention, if there is no conflict.

Figure 5A:
FIGS. 5A to 5F illustrate the states of the elastic material and the elastic non-woven fabrics of the present invention under various stretched, shrunk or natural widths, respectively.
Figure 5B:
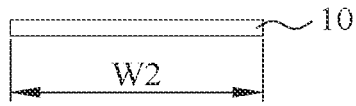
Figure 5C:
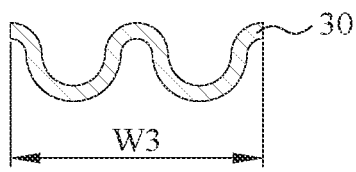
Figure 5D:
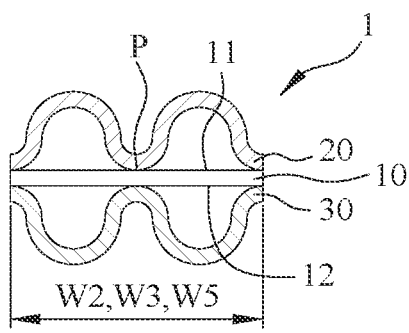

In order to achieve the forgoing objectives, the present invention provides an elastic composite non-woven fabric and the manufacturing equipment and manufacturing method thereof, wherein an elastic composite non-woven fabric 1 is manufactured by bonding pre-shrunk elastic non-woven fabrics 20 and 30 and an elastic material 10 together (as shown in FIG. 5D).

Figure 2:
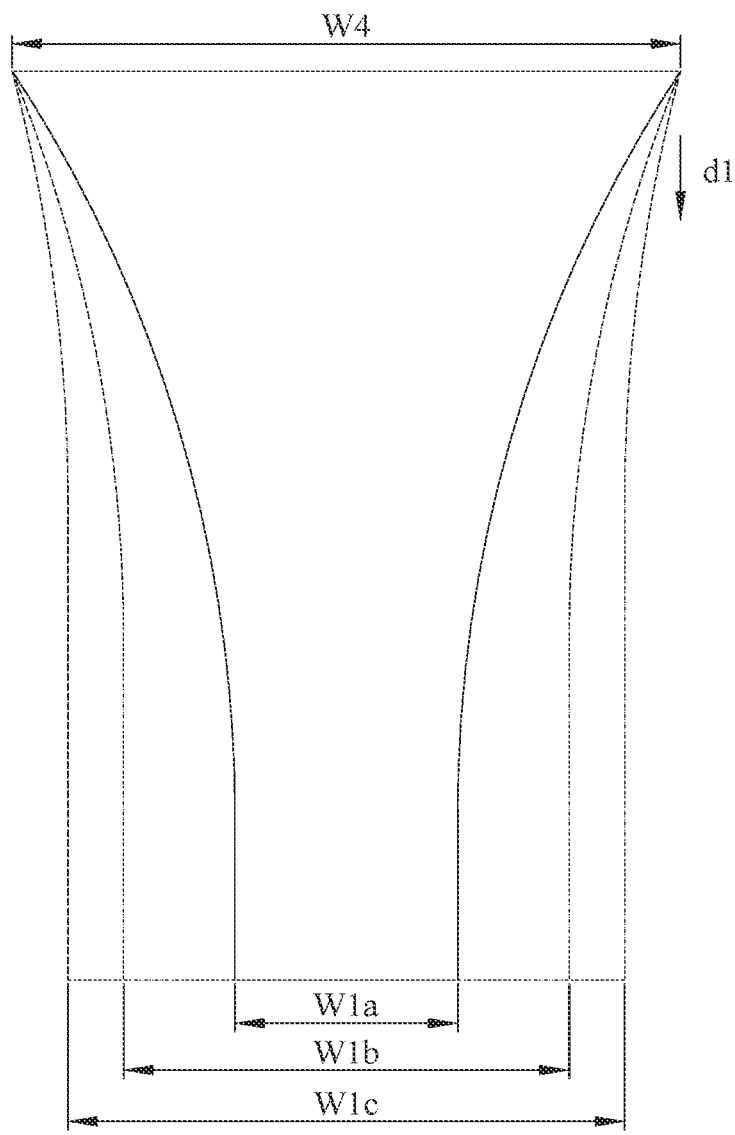
FIG. 2 illustrates a schematic diagram of the process of manufacturing elastic non-woven fabrics with different elongation by heat contraction as used in the present invention.

Referring to FIG. 2, which illustrates a schematic diagram of the process of manufacturing elastic non-woven fabrics with different elongation by heat contraction as used in the present invention. The elastic non-woven fabrics 20 and 30 as used in the present invention are formed by processing ordinary inelastic non-woven fabrics through heat contraction technique to impart extensibility to the non-woven fabrics. Specifically, the ordinary non-woven fabrics can be fed to a heat contraction device along a first direction d1, such that the ordinary non-woven fabrics contracts from its original width (e.g., W4 of FIG. 2) to a heat contracted width W1 (e.g., W1a, W1b, or W1c of FIG. 2) in the cross direction; wherein the original width of the ordinary non-woven fabrics is 1.5 to 3 times the heat contracted width.

Then, the formed elastic non-woven fabrics 20 and 30 can be stretched from the natural width thereof to a width equal to the original width of the ordinary non-woven fabrics. Accordingly, the elastic non-woven fabrics 20 and 30 can be stretched to a width of 1.5 to 3 times the natural width thereof, that is, they have an elongation of 50 to 200%.

Therefore, the natural width of the elastic non-woven fabrics 20 and 30 is defined as a first natural width W1. The width of the elastic non-woven fabrics 20 and 30 in a state of being stretched to 1.5 to 3 times the natural width thereof is defined as a first stretched width W4. In other words, the original width of the ordinary non-woven fabrics is equal to the stretched width W4 of the elastic non-woven fabrics 20 and 30 after being heat-contracted, while the heat-contracted width of the ordinary non-woven fabrics is equal to the natural width W1 of the elastic non-woven fabrics 20 and 30 after being heat-contracted.

As shown in FIG. 2, in specific embodiments, the elastic non-woven fabrics 20 and 30 each having different elongation (50%, 100%, 200%) can be stretched to 1.5 times, 2 times, or 3 times the natural width thereof, respectively, and thus can be stretched from the first natural width W1a, W1b, or W1c to the first stretched width W4, respectively.

The above-mentioned heat contraction process and heat contraction device for processing ordinary non-woven fabrics into elastic non-woven fabrics are specifically disclosed in U.S. Pat. No. 5,244,482, wherein the heat contraction device includes an oven, and front and rear conveying rollers with a certain proportion of speed difference, therefore, the ordinary non-woven fabrics can be processed into elastic non-woven fabrics through heat contraction.

Figure 3:
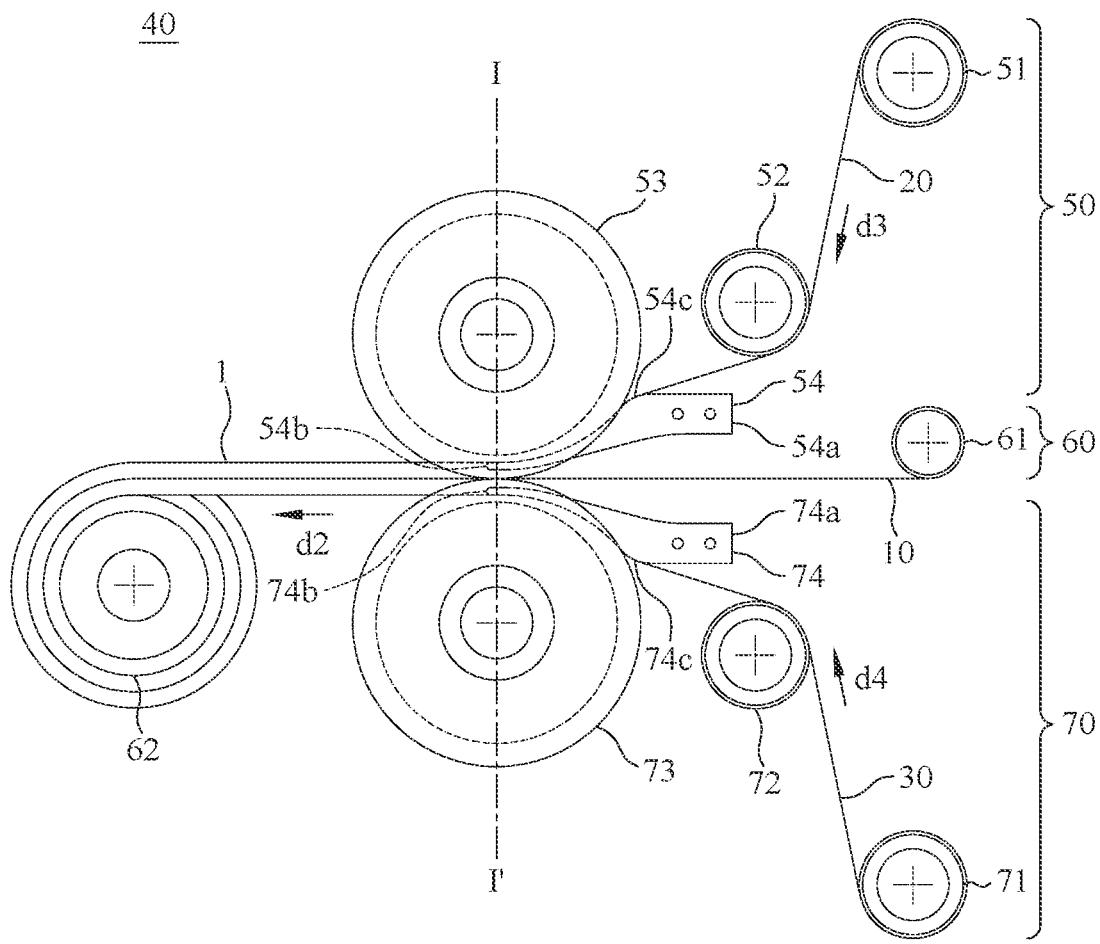
FIG. 3 illustrates a front view of the manufacturing equipment for an elastic composite non-woven fabric of the present invention.

Referring to FIG. 3, which illustrates a front view of a manufacturing equipment 40 for the elastic composite non-woven fabric of the present invention, wherein for the convenience of illustration, the housing or frame is not shown. The manufacturing equipment 40 for the elastic composite non-woven fabric provided by the present invention comprises: an upper part 50, which is provided with an upper feed roller 51, an upper shrink roller 52, an upper bonding roller 53, and a plurality of upper fins 54; a middle part 60, which is provided with a middle feed roller 61 and a winding roller 62; and a lower part 70, which is provided with a lower feed roller 71, a lower shrink roller 72, a lower bonding roller 73, and a plurality of lower fins 74.

In the manufacturing equipment 40 for the elastic composite non-woven fabric of the present invention, the elastic composite non-woven fabric of the present invention is formed by using the upper shrink roller 52 and the lower shrink roller 72 to pre-shrink the elastic non-woven fabric, and using the upper bonding roller 53 and the lower bonding roller 73 as clamps to bond the pre-shrunk elastic non-woven fabrics to the elastic material, wherein the additional use of the upper fins 54 and the lower fins 74 allows the elastic non-woven fabrics to be bond to the elastic material in a state of having regular wavy folds after being wavy inwardly arranged.

Preferably, relative to the middle part 60 (especially relative to the elastic material 10 at the middle part 60), the upper feed roller 51, the upper shrink roller 52, the upper bonding roller 53, and the upper fins 54 are arranged symmetrically with the lower feed roller 71, the lower shrink roller 72, the lower bonding roller 73, and the lower fins 74, respectively. Preferably, the upper feed roller 51, the upper shrink roller 52, the upper bonding roller 53, the middle feed roller 61, the winding roller 62, the lower feed roller 71, the lower shrink roller 72, and the lower bonding roller 73 are arranged in parallel to each other.

Figure 4A:
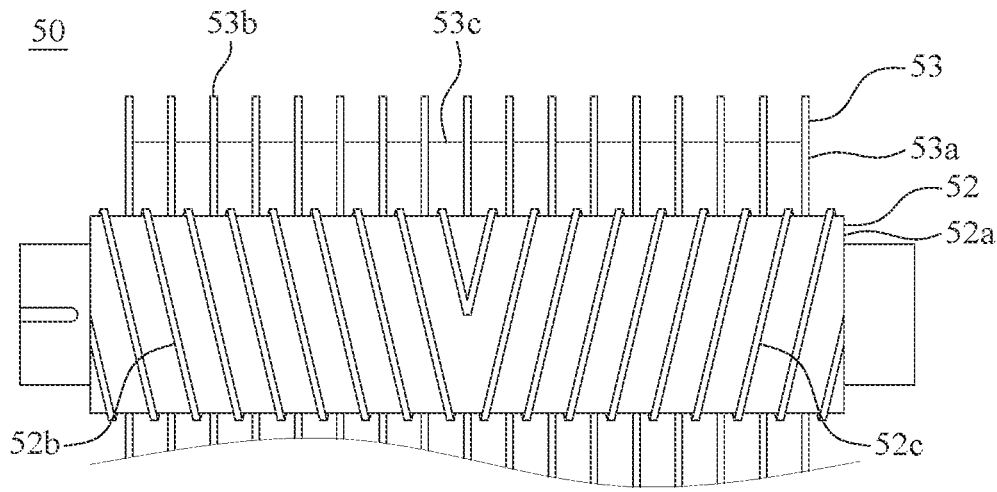
FIG. 4A illustrates a side view of the upper part of the manufacturing equipment for the elastic composite non-woven fabric of the present invention, viewed from the right side of FIG. 3.

Referring to FIG. 4A, which illustrates a side view of the upper part 50 of the manufacturing equipment 40 for the elastic composite non-woven fabric of the present invention, viewed from the right side of FIG. 3, wherein for the convenience of illustration, the first elastic non-woven fabric 20 and the upper feed roller 51 are not shown. The upper shrink roller 52 includes: a body 52a, which is in a column shape; and a first thread 52b and a second thread 52c, which are disposed on the body 52a, and arranged symmetrically with respect to the mid-perpendicular plane of the longitudinal axis of the upper shrink roller 52. The upper bonding roller 53 includes: a main body 53a, which is in a column shape; a plurality of teeth 53b (convex surfaces), which are provided, in parallel to each other at a fixed interval, on the outer peripheral surface of the main body 53a, and perpendicular to the longitudinal axis of the upper bonding roller 53; and a plurality of grooves 53c (concave surfaces), which are formed in a portion of the upper bonding roller 53 where the teeth 53b are not disposed.

Figure 4B:
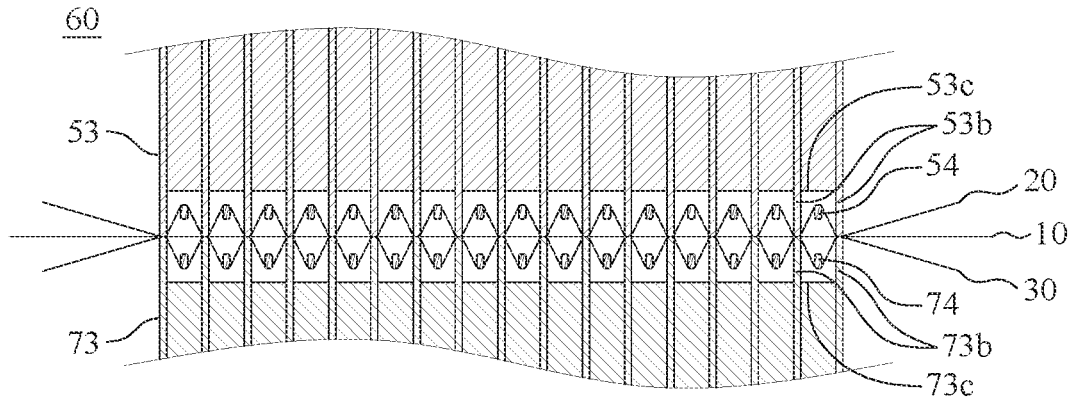
FIG. 4B illustrates a cross-sectional view of the middle part of the manufacturing equipment for the elastic composite non-woven fabric of the present invention taken along line I-I' of FIG. 3.

Referring to FIGS. 3 and 4B, FIG. 4B illustrates a cross-sectional view of the middle part 60 of the manufacturing equipment 40 for the elastic composite non-woven fabric of the present invention taken along line I-I' of FIG. 3 (viewed from the right side). The upper fins 54 and the lower fins 74 are each in a flat shape, and are each preferably metal fin.

The upper fins 54 each includes: a first end 54a pivotally fixed to the manufacturing equipment 40 for the elastic composite non-woven fabric; a second end 54b disposed in a corresponding one of the grooves 53c of the upper bonding roller 53; and a shoulder 54c disposed between the first end 54a and the second end 54b. The contour of each upper fin 54 from the shoulder 54c to the second end 54b substantially matches the contour of the outer peripheral surface of the main body 53a of the upper bonding roller 53.

The lower fins 74 each includes: a first end 74a pivotally fixed to the manufacturing equipment 40 for the elastic composite non-woven fabric; a second end 74b disposed in a corresponding one of the grooves 73c of the lower bonding roller 73; and a shoulder 74c disposed between the first end 74a and the second end 74b. The contour of each lower fin 74 from the shoulder 74c to the second end 74b substantially matches the contour of the outer peripheral surface of the main body 73a of the lower bonding roller 73.

Figure 4C:
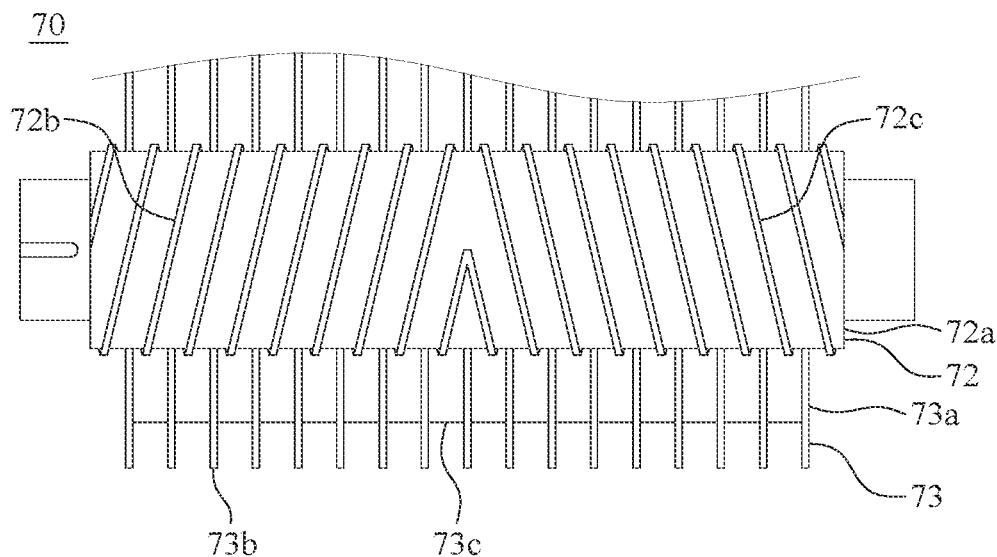
FIG. 4C illustrates a side view of the lower part of the manufacturing equipment for the elastic composite non-woven fabric of the present invention, viewed from the right side of FIG. 3.

Referring to FIG. 4C, which illustrates a side view of the lower part 70 of the manufacturing equipment 40 for the elastic composite non-woven fabric of the present invention, viewed from the right side of FIG. 3, wherein for the convenience of illustration, the second elastic non-woven fabric 30 and the lower feed roller 71 are not shown. The lower shrink roller 72 includes: a body 72a, which is in a column shape; and a first thread 72b and a second thread 72c, which are disposed on the body 72a, and arranged symmetrically with respect to the mid-perpendicular plane of the longitudinal axis of the lower shrink roller 72. The lower bonding roller 73 includes: a main body 73a, which is in a column shape; a plurality of teeth 73b (convex surfaces), which are provided, in parallel to each other at a fixed interval, on the outer peripheral surface of the main body 73a, and perpendicular to the longitudinal axis of the lower bonding roller 73; and a plurality of grooves 73c (concave surfaces), which are formed in a portion of the lower bonding roller 73 where the teeth 73b are not disposed.

As shown in FIG. 3, the middle feed roller 61, the upper feed roller 51, and the lower feed roller 71 feed the elastic material 10, the first elastic non-woven fabric 20, and the second elastic non-woven fabric 30 along a second direction d2, a third direction d3 and a fourth direction d4, respectively.

As shown in FIGS. 3 and 4A, the upper shrink roller 52 receives the first elastic non-woven fabric 20 from the upper feed roller 51, such that the first elastic non-woven fabric 20 enters the upper shrink roller 52 along the third direction d3. Then, the first thread 52b and the second thread 52c of the upper shrink roller 52 are symmetrically arranged, so that the upper shrink roller 52 drives the first elastic non-woven fabric 20 to shrink toward the center thereof at a steady speed along a direction parallel to the upper shrink roller 52, thereby the first elastic non-woven fabric 20 enters gaps among the upper fins 54 and the grooves 53c and the teeth 53b of the upper bonding roller 53 in a state of being not stretched by an external force, so that the first elastic non-woven fabric 20 is wavy inwardly arranged and formed with regular wavy folds, thereby the first elastic non-woven fabric 20 shrinks from the first natural width W1 to a first shrunk width W3.

As shown in FIGS. 3 and 4C, the lower shrink roller 72 receives the second elastic non-woven fabric 30 from the lower feed roller 71, such that the second elastic non-woven fabric 30 enters the lower shrink roller 72 along the fourth direction d4. Then, the first thread 72b and the second thread 72c of the lower shrink roller 72 are symmetrically arranged, so that the lower shrink roller 72 drives the second elastic non-woven fabric 30 toward the center thereof at a steady speed along a direction parallel to the lower shrink roller 72, thereby the second elastic non-woven fabric 30 enters gaps among the lower fins 74 and the grooves 73c and the teeth 73b of the lower bonding roller 73 in a state of being not stretched by an external force, so that the second elastic non-woven fabric 30 is wavy inwardly arranged and formed with regular wavy folds, thereby the second elastic non-woven fabric 30 shrinks from the first natural width W1 to the first shrunk width W3.

It is noted that a rotational speed of the upper feed roller 51, the upper shrink roller 52, the lower feed roller 71 and the lower shrink roller 72 is greater than that of the upper bonding roller 53 and the lower bonding roller 73, thereby resulting a speed difference. The first elastic non-woven fabric 20 and the second elastic non-woven fabric 30 can be effectively introduced between the upper fins 54 and the lower fins 74 due to this speed difference.

Figure 6A:
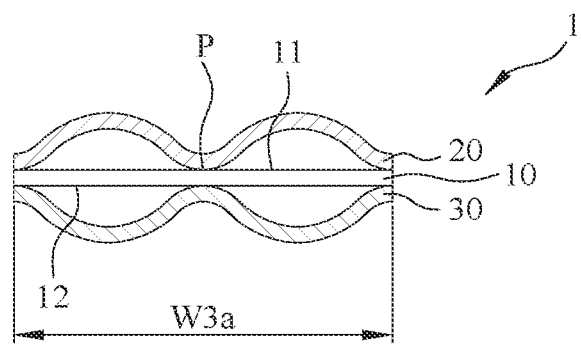
FIGS. 6A to 6C illustrate the embodiments of the elastic composite non-woven fabrics with different wave shapes, respectively.
Figure 6B:
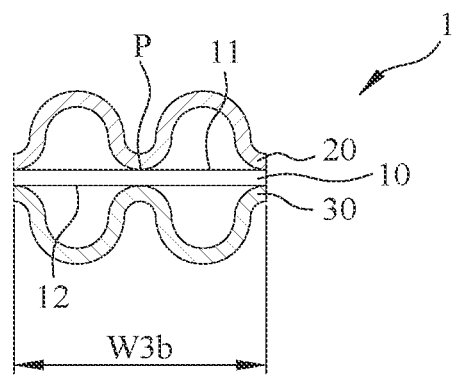
Figure 6C:
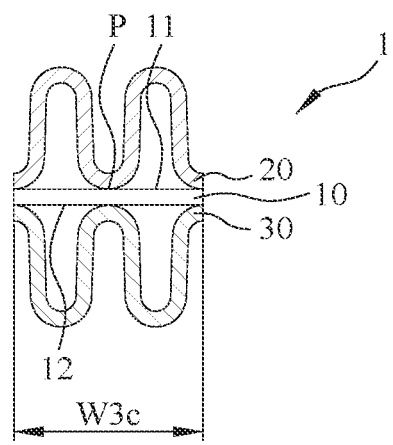

Preferably, a space between adjacent teeth 53b of the upper bonding roller 53 and a space between adjacent teeth 73b of the lower bonding roller 73 are adjustable, and/or a space between corresponding upper fin 54 and lower fin 74 is adjustable, so that the first elastic non-woven fabric 20 and the second elastic non-woven fabric 30 may have wave shapes with different height states as shown in FIGS. 6A to 6C, wherein the first shrunk width W3 of the first elastic non-woven fabric 20 and the second elastic non-woven fabric 30 may be W3a, W3b, or W3c.

Then, as shown in FIGS. 3 and 4B, the teeth 53b of the upper bonding roller 53 and the teeth 73b of the lower bonding roller 73 are aligned and adjacently disposed, respectively, such that the first elastic non-woven fabric 20 pre-shrunk and formed with the regular wavy folds, the elastic material 10 fed by the middle feed roller 61, and the second elastic non-woven fabric 30 pre-shrunk and formed with the regular wavy folds are bonded together at a portion where the teeth 53b of the upper bonding roller 53 and the teeth 73b of the lower bonding roller 73 are contacted, thereby forming the elastic composite non-woven fabric 1. Finally, the winding roller 62 winds the elastic composite non-woven fabric 1 after bonding for collection, so as to roll the elastic composite non-woven fabric 1 into a cylindrical shape.

Referring to FIG. 5D, which illustrates the elastic composite non-woven fabric 1 formed by bonding the pre-shrunk elastic non-woven fabrics 20 and 30 and the elastic material 10 of the present invention together. The elastic composite non-woven fabric 1 provided by the present invention comprises: an elastic material 10, which is in a planar shape, and includes an elastic film, an elastomeric non-woven fabric, or a combination thereof, and a first elastic non-woven fabric 20 and a second elastic non-woven fabric 30, which are wavy inwardly arranged and formed with regular wavy folds. Wherein the first elastic non-woven fabric 20 and the second elastic non-woven fabric 30 are respectively bonded to an upper surface 11 and a lower surface 12 of the elastic material 10 in a manner that the first elastic non-woven fabric 20 and the second elastic non-woven fabric 30 each are pre-shrunk and formed with the regular wavy folds, wherein the wavy folds of the first elastic non-woven fabric 20 and the second elastic non-woven fabric 30 are aligned and symmetrical to each other relative to the elastic material 10.

Referring to FIGS. 5A to 5F, which illustrate the states of the elastic non-woven fabrics 20 and 30 and the elastic material 10 used in the present invention under various stretched, shrunk or natural widths, respectively (in which the relative size relationships of the various widths are also shown).

As shown in FIGS. 5A and 5B, the natural width of the elastic non-woven fabrics 20 and 30 is defined as a first natural width W1, and the natural width of the elastic material 10 is defined as a second natural width W2.

As shown in FIG. 5C (in which the elastic non-woven fabric 30 is take as an example), the elastic non-woven fabrics 20 and 30 are pre-shrunk to a width equal to the second natural width W2 of the elastic material 10, and such width is defined as the first shrunk width W3.

Then, as shown in FIG. 5D, the elastic non-woven fabrics 20 and 30 are respectively bonded, in a state of being pre-shrunk to the first shrunk width W3 to have a wave shape, to the upper surface 11 and the lower surface 12 of the elastic material 10 maintained at the second natural width W2, thereby forming the elastic composite non-woven fabric 1. The natural width of the elastic composite non-woven fabric 1 is defined as a third natural width W5. There are a plurality of bonding points P between the elastic non-woven fabrics 20 and 30 and the elastic material 10.

Figure 5E:
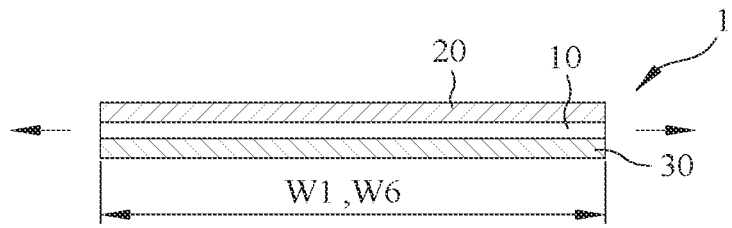

After that, the elastic composite non-woven fabric 1 can be stretched, so that the elastic non-woven fabrics 20 and 30 located on its upper surface 11 and lower surface 12 changes from a wavy state (as shown in FIG. 5D) to a flat state (as shown in FIG. 5E), the width of the elastic composite non-woven fabric 1 at this time is defined as a second stretched width W6. The second stretched width W6 is equal to the first natural width W1 of the elastic non-woven fabrics 20 and 30 before shrinking. During the stretching of the elastic composite non-woven fabric 1 from the third natural width W5 (as shown in FIG. 5D) to the second stretched width W6 (as shown in FIG. 5E), the tensile property of the elastic composite non-woven fabric 1 is provided only by the elastic material 10, therefore, it will exhibit the characteristics of low initial tension (that is, the elastic composite non-woven fabric is softer and easier to be stretched in this process), this process is hereinafter referred to as a first-stage stretching.

Figure 5F:
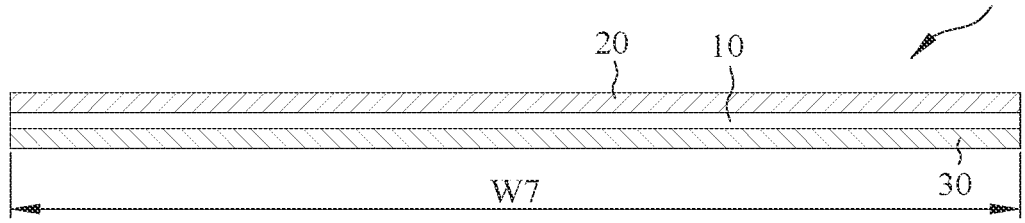

Then, the stretching of the elastic composite non-woven fabric 1 can be continued, so that the elastic non-woven fabrics 20 and 30 can reach the actual ultimate stretched width, thereby the elastic composite non-woven fabric 1 is stretched from the second stretched width W6 (as shown in FIG. 5E) to an ultimate stretched width W7 (as shown in FIG. 5F), this process is hereinafter referred to as a second-stage stretching.

During the stretching of the elastic composite non-woven fabric 1 from the second stretched width W6 (as shown in FIG. 5E) to the ultimate stretched width W7 (as shown in FIG. 5F), the elastic composite non-woven fabric 1 is further stretched beyond the second stretched width W6 due to its elasticity, the elastic material 10 does not reach its ultimate stretched width, while the elastic composite non-woven fabric 1 can be stretched to its ultimate stretched width W7.

In other words, the cross-direction ultimate stretched width W7 of the elastic composite non-woven fabric 1 is equal to the cross-direction ultimate stretched width W4 of the elastic non-woven fabrics 20 and 30, but less than the cross-direction ultimate stretched width of the elastic material 10.

Theoretically, the ultimate stretched width of the elastic composite non-woven fabric 1 should be equal to the ultimate stretched width of the elastic non-woven fabrics 20 and 30. However, in practice, the bonding of the elastic material 10 and the elastic non-woven fabrics 20 and 30 will cause a part of the material to lose its extensibility, thus, the ultimate stretched width W7 of the elastic composite non-woven fabric 1 is only about 90 to 95% of the theoretical ultimate stretched width (that is, the first stretched width W4) of the elastic non-woven fabrics 20 and 30.

During the stretching of the elastic composite non-woven fabric 1 from the second stretched width W6 (as shown in FIG. 5E) to the ultimate stretched width W7 (as shown in FIG. 5F), the tensile strength of the elastic composite non-woven fabric 1 is provided by the elastic non-woven fabrics 20 and 30 together with the elastic material 10, thus, it will exhibit the characteristics of high recovery force and high tensile strength (that is, it is relatively not easier to be stretched, but easier to contract in this process).

At the same time, in the present invention, the ordinary non-woven fabric is heat-contracted into elastic non-woven fabrics 20 and 30 with extensibility through heat contraction process first (first-stage contraction), then the elastic non-woven fabrics 20 and 30 shrink inward into wave shapes by a pre-shrinking step (e.g., using the manufacturing equipment 40 for the elastic composite non-woven fabric of the present invention) (second-stage shrinking), and finally the elastic non-woven fabrics 20 and 30 are bonded to the elastic material 10 to form the elastic composite non-woven fabric 1. Thus, the natural width of the elastic composite non-woven fabric 1 can be much less than the natural width of the elastic composite non-woven fabric of the prior art, therefore, it can exhibit high stretchability and high recovery force.

The recovery force and deformation rate of the elastic composite non-woven fabric 1 depend on the type of the elastic material 10 used.

Preferably, the elastic film of the elastic material 10 of the present invention comprises at least one of: a polystyrene copolymer material including at least one of styrene-butadiene block copolymer, styrene-ethylene-butylene-styrene block copolymer (SEBS) and thermoplastic polyolefin elastomer (TPO); and thermoplastic polystyrene elastomer (TPS).

It is well known that the thermoplastic polystyrene elastomers (TPS) mentioned above, which are also referred to as styreneic block copolymers (SBCs), are a type of thermoplastic elastomer with the largest production currently in the world and having the properties most similar to that of rubber. Currently, there are mainly four types in the species of the thermoplastic polystyrene elastomer series, that is: styrene-butadiene-styrene block copolymer (SBS), styrene-isoprene-styrene block copolymer (SIS), styrene-ethylene-butylene-styrene block copolymer (SEBS) and styrene-ethylene-propylene-styrene block copolymer (SEPS), wherein SEBS and SEPS are hydrogenated copolymers of SBS and SIS, respectively.

Further, the hard segment of the thermoplastic polyolefin elastomer (TPO) is a polyolefin material such as polypropylene (PP) or polyethylene (PE) or the like, wherein the soft segment thereof is a rubber such as ethylene propylene diene monomer (EPDM) and the like. Generally, TPO is formed by polymerization using metallocene as a catalyst, wherein the hard segment portion and the soft segment portion are directly combined by a covalent bond, and thus TPO is also referred to as M-POE.

Preferably, at least one of the first elastic non-woven fabric 20 and the second elastic non-woven fabric 30 of the present invention includes at least one of polypropylene fiber, polyethylene fiber, and polylactic acid fiber. An ordinary non-woven fabric made from the above-mentioned components can form an elastic non-woven fabric with an elongation of 50 to 200% after the heat contraction process.

Preferably, the elastomeric non-woven fabric of the elastic material 10 of the present invention comprises: 5 to 55 wt % of a polymer material fiber as substrate, which includes at least one of polypropylene and polyethylene, and can be spunbond, meltblown or air-through non-woven fabric; and 40 to 90 wt % of an elastomer, wherein the elastomer comprises at least one of: a polystyrene copolymer material including at least one of styrene-butadiene block copolymer, styrene-ethylene-butylene-styrene block copolymer (SEBS) and thermoplastic polyolefin elastomer (TPO); and thermoplastic polystyrene elastomer (TPS).

In the embodiment in which the elastomeric non-woven fabric is used as the elastic material 10, it is possible to impart the elastic composite non-woven fabric 1 with both elastic and breathable properties.

The first elastic non-woven fabric 20 and the second elastic non-woven fabric 30 of the present invention each have an elongation of 50 to 200%, that is, they can each be stretched to a width of 1.5 to 3 times the natural width thereof.

In some embodiments, the first elastic non-woven fabric 20 and the second elastic non-woven fabric 30 each have a shrinkage of 33.3% to 66.7%, that is, their widths after being wavy inwardly arranged are ⅓ to ⅔ times the natural width thereof, respectively.

In other embodiments, the first elastic non-woven fabric 20 and the second elastic non-woven fabric 30 each have a shrinkage of 50% to 85%, that is, their widths after being wavy inwardly arranged are 0.15 to 0.5 times the natural width thereof, respectively.

Preferably, the elastic material 10 of the present invention has an elongation of 600 to 1300%, that is, it can be stretched to a width of 7 to 13 times the natural width thereof.

In some embodiments, the elastic composite non-woven fabric 1 of the present invention has an elongation of 250 to 800%, that is, it can be stretched to a width of 3.5 to 9 times the natural width thereof.

In other embodiments, the elastic composite non-woven fabric 1 of the present invention has an elongation of 300 to 1000%, that is, it can be stretched to a width of 4 to 11 times the natural width thereof.

In the ideal embodiment, the elastic material 10 has an elongation of 900%, that is, it can be stretched to a width of 10 times the natural width thereof. The elastic non-woven fabrics 20 and 30 are bonded, in a state that the shrinkage thereof is 33.3% to 66.7% (that is, being shrunk to a width of ⅓ to ⅔ times the natural width thereof), to the elastic material 10 maintained at the (second) natural width W2, which indicates that in the first-stage stretching, the elastic composite non-woven fabric 1 can be stretched to a width of up to 3 times the natural width thereof. The elastic non-woven fabrics 20 and 30 have an elongation of 50 to 200%, that is, they can be stretched to a width of 1.5 to 3 times the natural width thereof, which indicates that in the second-stage stretching, the elastic composite non-woven fabric 1 can be stretched to a width of up to 3 times the second stretched width thereof. Accordingly, the elastic composite non-woven fabric 1 is imparted with the potential to be stretched to a width of up to totally 3×3=9 times the natural width thereof. However, because of the loss of elongation of about 5% due to bonding, the elastic composite non-woven fabric 1 reaches the ultimate stretched width W7 when being stretched to a width of 8.55 times the natural width thereof (that is, having an elongation of 755%).

In a more practical embodiment, the elastic material 10 has an elongation of 700%, that is, it can be stretched to a width of up to 8 times the natural width thereof. The elastic non-woven fabrics 20 and 30 are bonded, in a state that the shrinkage is 33.3 to 50% (that is, being shrunk to a width of ⅔ to ½ times the natural width thereof), to the elastic material 10 maintained at the (second) natural width W2, thereby forming the elastic composite non-woven fabric 1 with the (third) natural width W5, which indicates that in the first-stage stretching, the elastic composite non-woven fabric 1 can be stretched to a width of up to 2 times the natural width thereof. The elastic non-woven fabrics 20 and 30 have an elongation of 50 to 100%, that is, they can be stretched to a width of 1.5 to 2 times the natural width thereof, which indicates that in the second-stage stretching, the elastic composite non-woven fabric 1 can be stretched to a width of up to 2 times the second stretched width thereof. Accordingly, the elastic composite non-woven fabric 1 is imparted with the potential to be stretched to a width of totally 2×2=4 times the natural width thereof. However, because of the loss of elongation of 10% due to bonding, the elastic composite non-woven fabric 1 reaches the ultimate stretched width W7 when being stretched to a width of 3.6 times the natural width thereof (that is, having an elongation of 260%).

In a preferable embodiment, the elastic material 10 has an elongation of 700%, that is, it can be stretched to a width of 8 times the natural width thereof. The elastic non-woven fabrics 20 and 30 are bonded, in a state that the shrinkage is 50 to 66.7% (that is, being shrunk to a width of ½ to ⅓ times the natural width thereof), to the upper surface 11 and the lower surface 12 of the elastic material 10 maintained at the (second) natural width W2, thereby forming the elastic composite non-woven fabric 1 with the (third) natural width W5, indicating that in the first-stage stretching, the elastic composite non-woven fabric 1 can be stretched to a width of up to 3 times the natural width thereof. The elastic non-woven fabrics 20 and 30 have an elongation of 100%, that is, they can be stretched to a width of 2 times the natural width thereof, indicating that in the second-stage stretching, the elastic composite non-woven fabric 1 can be stretched to a width of up to 2 times the second stretched width thereof. Accordingly, the elastic composite non-woven fabric 1 is imparted with the potential to be stretched to a width of totally 3×2=6 times the natural width thereof. However, because of the loss of elongation of 10% due to bonding, the elastic composite non-woven fabric 1 reaches the ultimate stretched width W7 when being stretched to a width of 5.4 times the natural width thereof (that is, having an elongation of 440%).

Generally, the loss of elongation due to bonding is about 5 to 6% or 5 to 8%. However, depending on the bonding degree and the actual material used, the loss of elongation may be greater or less.

In the process of being stretched to the ultimate stretched width W7, the elastic material 10 can provide elastic contraction force, therefore the elastic composite non-woven fabric 1 can contract back to approximately the third natural width W5. The degree of contraction and recovery depends on the deformation rate of the elastic material 10 used.

For example, the ordinary non-woven fabric has an original width of 200 cm, which undergoes a heat contraction process to form elastic non-woven fabrics 20 and 30 with a (first) natural width W1 of 100 cm. Thus, the elastic non-woven fabrics 20 and 30 can be stretched to 2 times the natural width thereof (that is, they can be stretched to a width equal to the original width of ordinary non-woven fabric), i.e., 200 cm (that is, having an elongation of 100%). When the elastic non-woven fabrics 20 and 30 move to the space between the upper bonding roller 53 and the lower bonding roller 73 of the manufacturing equipment 40 for the elastic composite non-woven fabric, the elastic non-woven fabrics 20 and 30 are pre-shrunk to the first shrunk width W3, i.e., 50 cm (that is, having a shrinkage of 50%). At this time, the elastic non-woven fabrics 20 and 30, which are pre-shrunk to the first shrunk width W3 (that is, 50 cm), can be bonded to the elastic material 10 maintained at a second natural width W2 (that is, 50 cm). After leaving the upper bonding roller 53 and the lower bonding roller 73 of the manufacturing equipment 40 for the elastic composite non-woven fabric, the formed elastic composite non-woven fabric 1 has a third natural width W5, that is, 50 cm.

It is noted that, since the elastic non-woven fabrics 20 and 30 are bonded, in a state that the shrinkage is 50% (that is, being pre-shrink to ½ times the natural width), to the elastic material 10 maintained at the natural width, and the elastic non-woven fabrics 20 and 30 have an elongation of 100%, that is, they can be stretched to 2 times the natural width thereof (while the elastic material 10 has a elongation of 600%, that is, it can be stretched to 7 times natural width thereof), the elastic composite non-woven fabric 1 have the potential to be stretched to 4 times the natural width thereof (a stretching of 2 times of width can be provided during the stretching from the first shrunk width to the first natural width; and a stretching of additional 2 times of width can further be provided during the stretching from the first natural width to the first stretched width). However, because of the loss of elongation of 10% due to bonding, the elastic composite non-woven fabric 1 can only be stretched from its (third) natural width W5 (that is, 50 cm) to the ultimate stretched width W7 (that is, 200 cm×90%=180 cm). Meanwhile, the elastic material 10 can provide elastic contraction force, thus the elastic composite non-woven fabric 1 can be contracted back to the (third) natural width W5 (that is, about 50 cm). In this case, the elastic composite non-woven fabric can be recovered from an ultimate stretched width of 180 cm to a natural width of 50 cm (which is 28% of the ultimate stretched width), which has excellent recovery performance.

Figure 7:
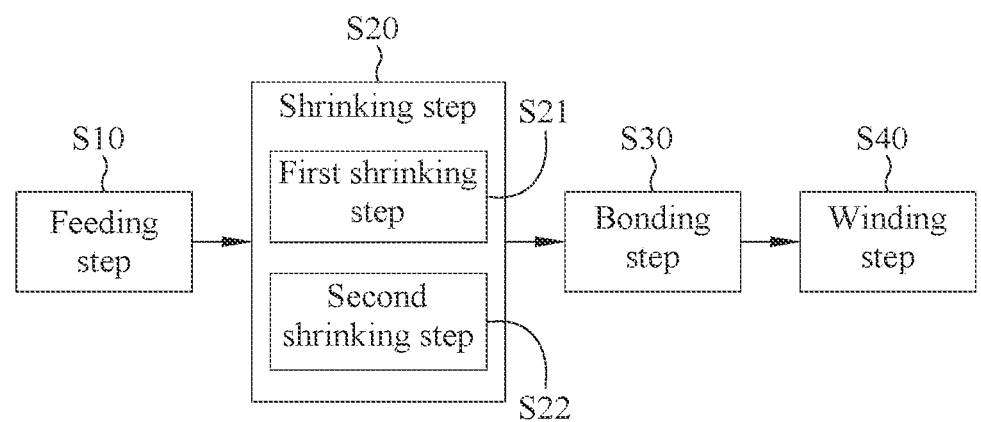
FIG. 7 illustrates a flow chart of the manufacturing method of the elastic composite non-woven fabric of the present invention.
Figure 8A:
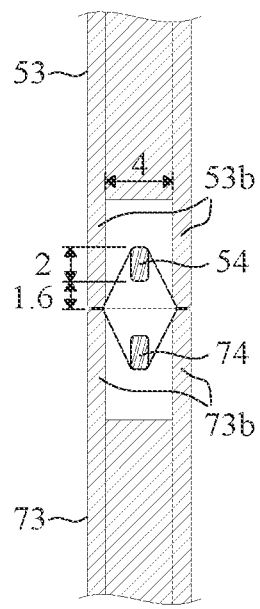
FIGS. 8A to 8D illustrate partial cross-sectional views of the middle parts of the manufacturing equipment for the elastic composite non-woven fabric taken along line I-I' of FIG. 3 according to Examples 1 to 4 of the present invention, respectively; wherein only one set of corresponding grooves, teeth adjacent to the grooves, and corresponding fins are shown.
Figure 8B:
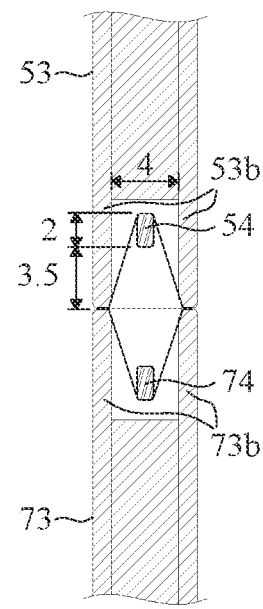
Figure 8C:
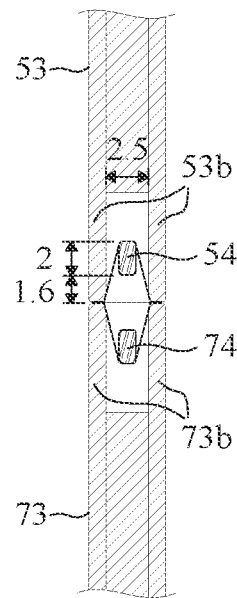
Figure 8D:
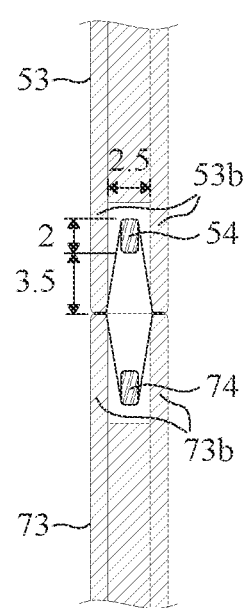
Figure 9:
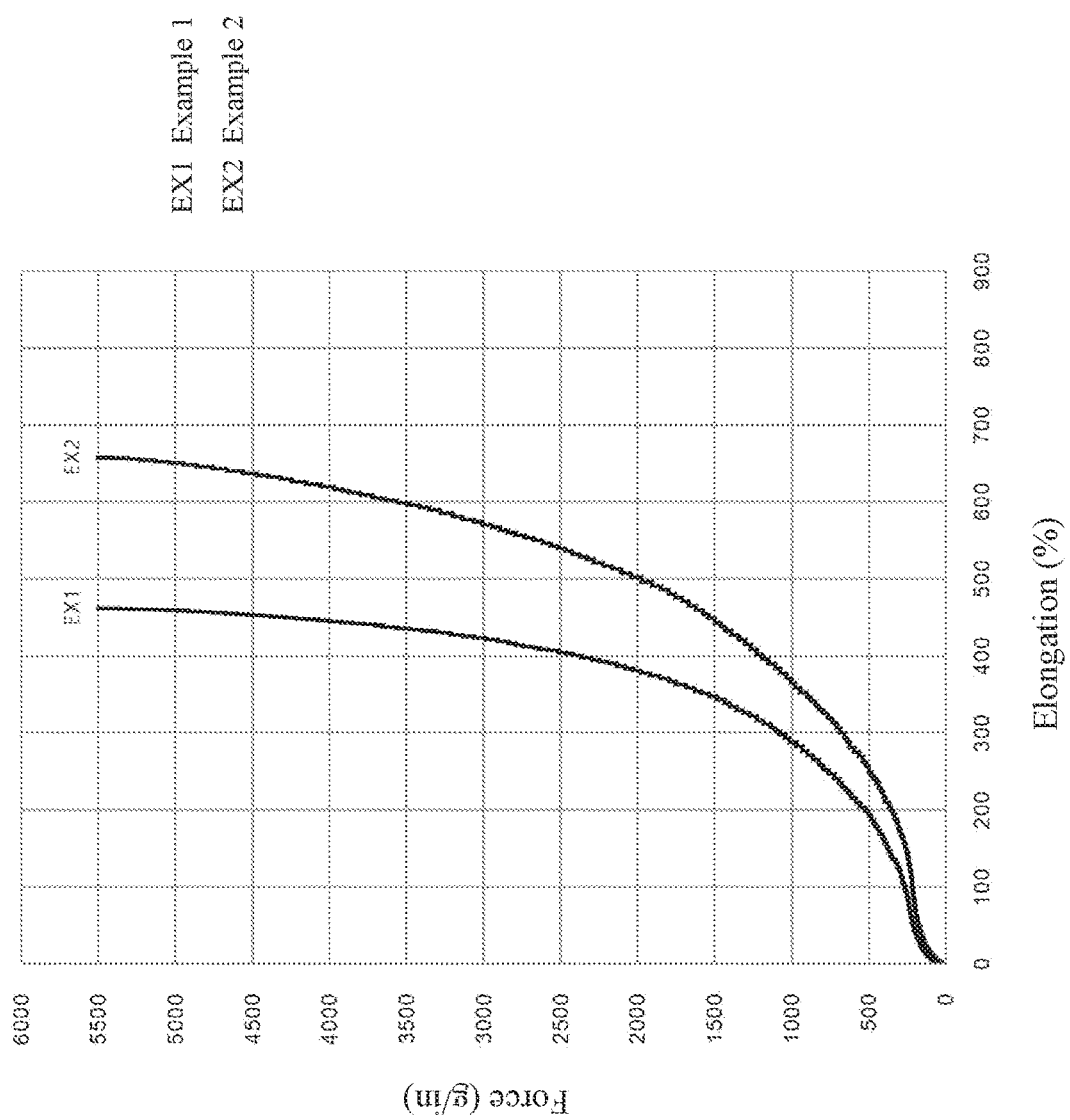
FIG. 9 illustrates the results of tensile test for the elastic composite non-woven fabrics according to Examples 1 and 2 of the present invention.
Figure 10:
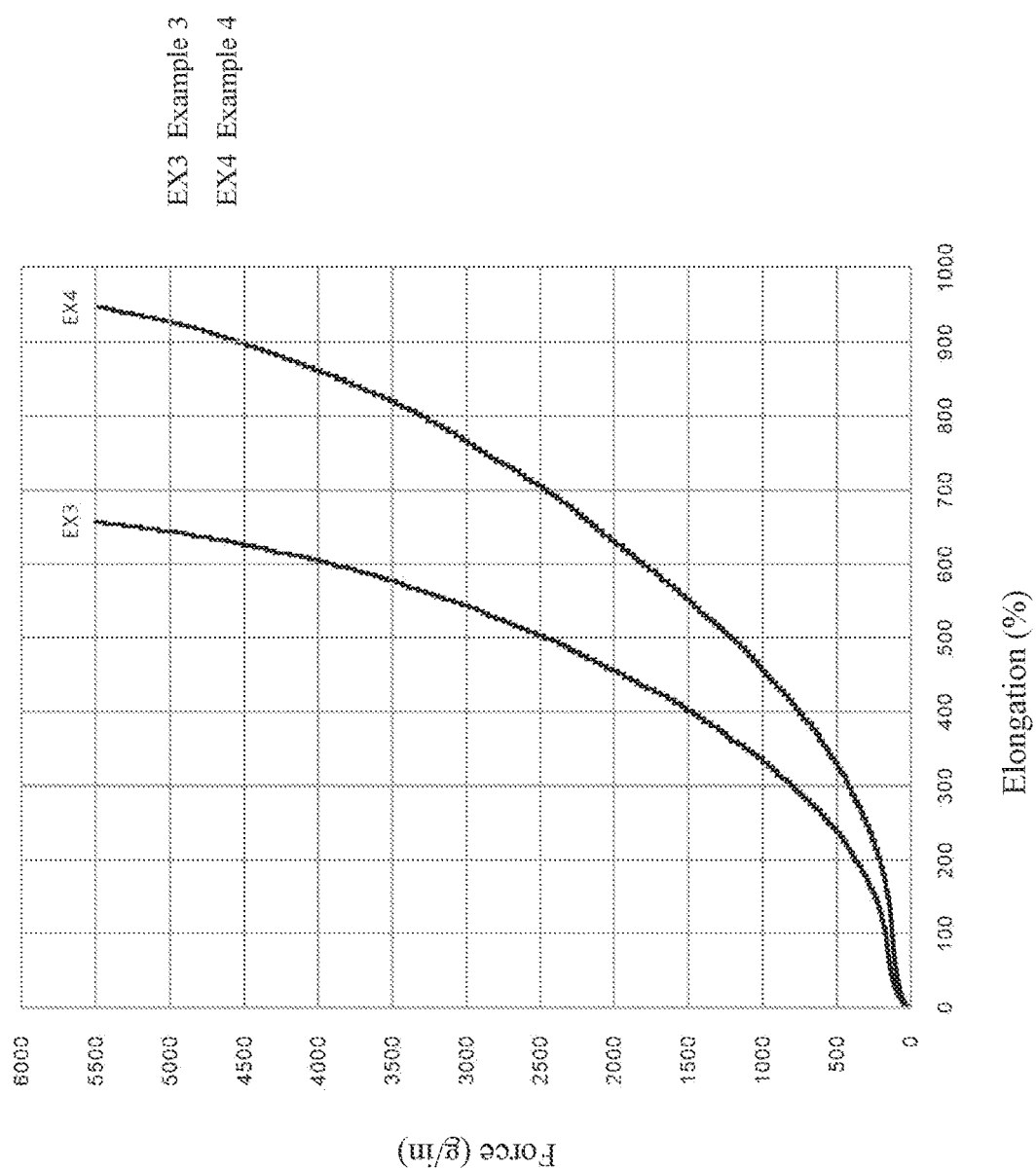
FIG. 10 illustrates the results of tensile test for the elastic composite non-woven fabrics according to Examples 3 and 4 of the present invention.
Figure 11:
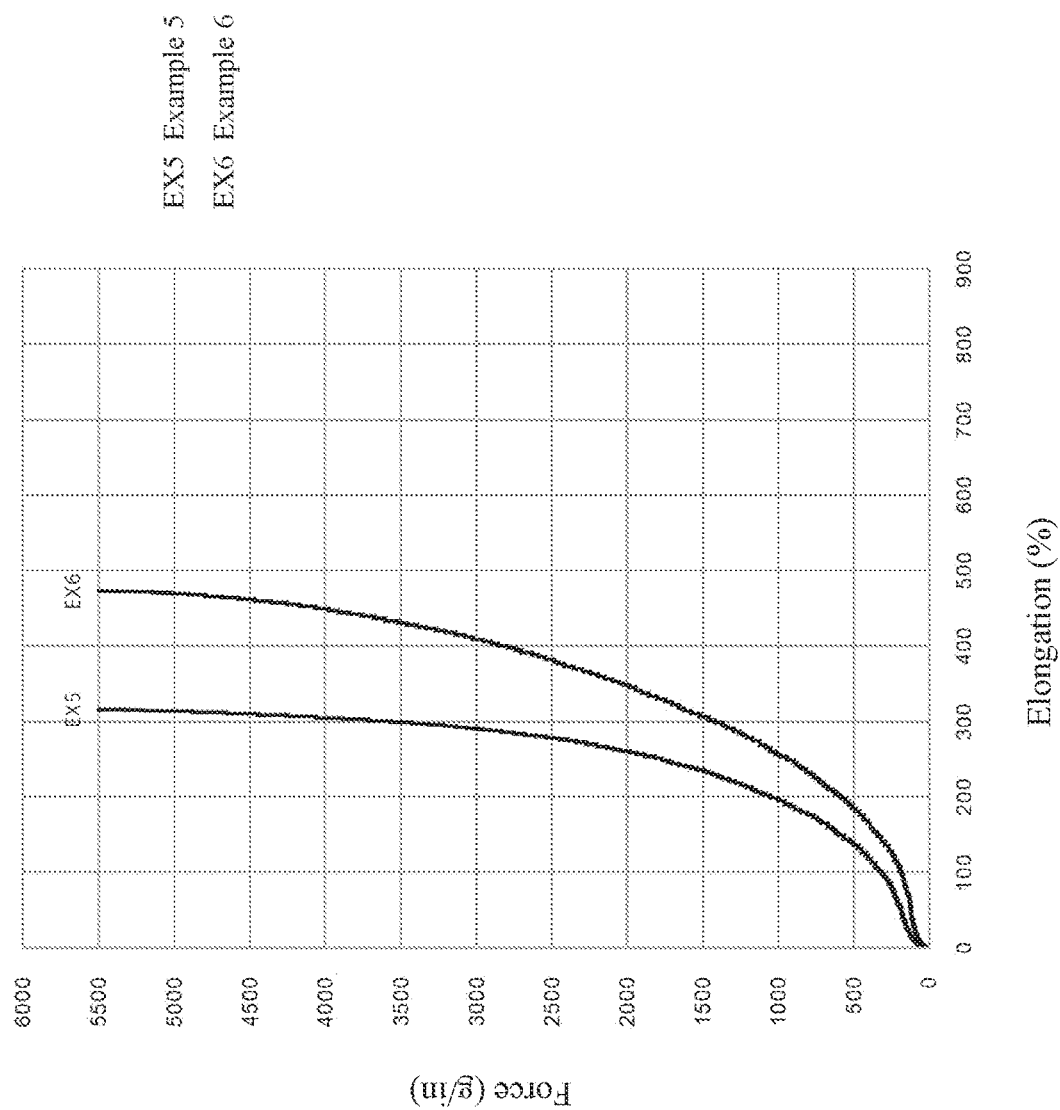
FIG. 11 illustrates the results of tensile test for the elastic composite non-woven fabrics according to Examples 5 and 6 of the present invention.

Referring to FIG. 7, which illustrates a flow chart of the manufacturing method of the elastic composite non-woven fabric of the present invention. The manufacturing method of an elastic composite non-woven fabric provided by the present invention includes a feeding step S10, a shrinking step S20, and a bonding step S30.

In the feeding step S10, a first elastic non-woven fabric, an elastic material, and a second elastic non-woven fabric are fed by an upper feed roller 51, a middle feed roller 61, and a lower feed roller 71 of the manufacturing equipment 40 for the elastic composite non-woven fabric, respectively. Specifically, in order to feed the elastic material, the elastic material is moved along the second direction in a state of maintained at the second natural width W2 (for example, the elastic material is fed to the manufacturing equipment 40 for the elastic composite non-woven fabric of the present invention and then clamped by the upper bonding roller 53 and the lower bonding roller 73); and in order to feed the first and second elastic non-woven fabrics, the first and second elastic non-woven fabrics are moved along the third direction and the fourth direction respectively (for example, the first and second elastic non-woven fabrics are fed to the upper shrink roller 52 and the lower shrink roller 72 of the manufacturing equipment 40 for the elastic composite non-woven fabric of the present invention, respectively).

The first elastic non-woven fabric and the second elastic non-woven fabric may be stretched to 1.5 to 3 times the natural widths thereof. The elastic material includes an elastic film, an elastomeric non-woven fabric, or a combination thereof.

The shrinking step S20 may include a first shrinking step S21 and a second shrinking step S22. The first shrinking step S21 and the second shrinking step S22 are preferably performed simultaneously.

In the first shrinking step S21, the first elastic non-woven fabric is wavy inwardly arranged and formed with regular wavy folds by the above-mentioned upper shrink roller, upper bonding roller, and a plurality of upper fins. Specifically, the first elastic non-woven fabric is moved along the third direction, and the upper shrink roller drives the first elastic non-woven fabric to shrink toward the center thereof in a direction parallel to the upper shrink roller at a steady speed by the symmetrically arranged first and second threads, thereby the first elastic non-woven fabric enters gaps among the upper fins and the grooves and the teeth of the upper bonding roller in a state without being stretched by an external force and advances smoothly, at the same time, it turns to the second direction which is the same as the feeding direction of the elastic material to form regular wavy folds.

In the second shrinking step S22, the second elastic non-woven fabric is wavy inwardly arranged and formed with regular wavy folds by the above-mentioned lower shrink roller, lower bonding roller, and a plurality of lower fins. Specifically, the second elastic non-woven fabric is moved along the fourth direction, and the lower shrink roller drives the second elastic non-woven fabric to shrink toward the center thereof in a direction parallel to the lower shrink roller at a steady speed by the symmetrically arranged first and second threads, thereby the second elastic non-woven fabric enters gaps among the lower fins and the grooves and the teeth of the lower bonding roller in a state without being stretched by an external force and advances smoothly, at the same time, it turns to the second direction which is the same as the feeding direction of the elastic material to form regular wavy folds.

After the shrinking step S20, the first elastic non-woven fabric and the second elastic non-woven fabric shrink to the first shrunk width W3 and sandwich the elastic material maintained at the second natural width W2, and then move in the second direction.

In the bonding step S30, the first elastic composite non-woven fabric, the second elastic composite non-woven fabric, and the elastic material located therebetween, which move in the second direction, are clamped by the above-mentioned upper bonding roller and lower bonding roller, so that the first elastic non-woven fabric, the elastic material, and the second elastic non-woven fabric are bonded together to form a three-layer composite structure of first elastic composite non-woven fabric-elastic material-second elastic composite non-woven fabric, and move in the second direction. Specifically, the teeth of the upper bonding roller and the teeth of the lower bonding roller are aligned and adjacently disposed, respectively, such that the first elastic non-woven fabric pre-shrunk by the first shrinking step, the fed elastic material, and the second elastic non-woven fabric pre-shrunk by the second shrinking step are pressed and bonded together at a portion where the teeth of the upper bonding roller and the teeth of the lower bonding roller are contacted, thereby forming the elastic composite non-woven fabric; wherein, the plurality of upper fins and the plurality of lower fins are respectively inserted into the plurality of grooves of the upper and lower bonding rollers, in the non-contact area between the plurality of grooves, the first elastic non-woven fabric and the second elastic non-woven fabric are slowly shrunk to form waves due to the presence of the upper and lower fins.

In the manufacturing method of the elastic composite non-woven fabric of the present invention, the first elastic non-woven fabric after the first shrinking step and the second elastic non-woven fabric after the second shrinking step each have a shrinkage of 50 to 85%.

Preferably, in the manufacturing method of the elastic composite non-woven fabric according to the present invention, after the bonding step S30, a winding step S40 can be further comprised, wherein the elastic composite non-woven fabric is driven in the second direction, so as to wind the formed elastic composite non-woven fabric for collection, thereby the elastic composite non-woven fabric is rolled into a cylindrical shape.

Preferably, in the manufacturing method of the elastic composite non-woven fabric according to the present invention, a height or a width of the wavy folds of the first elastic non-woven fabric and the second elastic non-woven fabric are adjusted by adjusting a space between adjacent teeth of the upper bonding roller and a space between adjacent teeth of the lower bonding roller, and/or by adjusting a space between corresponding upper fin and lower fin. Specifically, by adjusting the positions of the upper and lower fins, the wave shape and the shrunk width of the first elastic non-woven fabric and the second elastic non-woven fabric can be changed.

Preferably, in the bonding step S30, the first elastic non-woven fabric, the elastic material, and the second elastic non-woven fabric can be bonded together by means of hot pressing or adhesive.

Preferably, in the bonding step S30, the first elastic non-woven fabric, the elastic material, and the second elastic non-woven fabric are bonded together by heating the teeth made of metal.

Preferably, according to different bonding types, the teeth of at least one of the upper bonding roller and the lower bonding roller may be additionally provided with a plurality of protrusions, such that a portion (for example, the bonding points P as shown in FIG. 5D) where the first elastic non-woven fabric, the elastic material, and the second elastic non-woven fabric are bonded together includes a plurality of points; alternatively, in a state without additionally providing protrusions, the bonding portion may be in the form of a line.

Preferably, before the bonding step S30, the surface or whole of the elastic material is coated with an adhesive (viscose); and in the bonding step S30, the first elastic non-woven fabric after the first shrinking step S21, the elastic material coated with the adhesive, and the second elastic non-woven fabric after the second shrinking step S22 are pressed and bonded together, thereby forming the elastic composite non-woven fabric.

Preferably, in the case of bonding by means of adhesive, the adhesive is usually directly sprayed on the surface of the elastic material and then bonded with the pre-shrunk elastic non-woven fabrics.

Preferably, the elastic material and elastic non-woven fabrics used in the manufacturing method of the elastic composite non-woven fabric according to the present invention may be the aforementioned elastic material 10 and elastic non-woven fabrics 20 and 30, respectively.

To verify the effect of the elastic composite non-woven fabric of the present invention, the composite non-woven fabrics of Examples 1 to 6 (EX1 to EX6) and Comparative Examples 1 to 2 (CE1 to CE2) were prepared with the parameters listed in columns 2 to 7 of Table 1 and subjected to tensile tests.

In Table 1, the fin space refers to the space between the corresponding upper and lower fins in I-I' plane, and the tooth space refers to the space between the adjacent teeth of the bonding roller.

Examples 1 to 6 were prepared as described in the above embodiments of the present invention, wherein a ½ fin space of 1.6 to 3.5 mm, a fin height of 2 mm (that is, the height of the fin in the I-I' plane along the up and down directions of FIG. 3), a tooth space of 2.5 to 4 mm, and a cutting width of 10 cm (large cut piece) were used, as shown in FIGS. 8A to 8D. Examples 5 and 6 are manufactured in the same manner as Examples 3 and 4, except that half of the cutting width (5 cm, small cut piece) relative to that of Examples 3 and 4 is used, respectively.

Comparative Example 1 is a type of composite non-woven fabric of the prior art, wherein by using a clamp, the elastic material is stretched and then bonded with upper and lower ordinary non-woven fabrics that has no stretchability, and the composite non-woven fabric is then loosened such that the elastic material contracts back and the ordinary non-woven fabric is formed with wavy folds.

Comparative example 2 is another type of composite non-woven fabric of the prior art, wherein a spunlace non-woven fabric prepared by high-pressure water column puncture is used as upper and lower non-woven fabrics (without stretchability), the non-woven fabrics are sprayed with adhesive and then bonded to the elastic material as the middle layer, and then the tissue of the non-woven fabric is broken by activation steps to be imparted with stretchability.

For Examples 1 to 6 and Comparative Examples 1 to 2, each material is tested with a tensile testing machine (Lloyd LR5KPlus) and load cell (Loadcells, XLC-0100-A1) using the same conditions as below with reference to ASTM D3776 and ASTM D882 standard methods.

For the large cut piece, the size of the specimen is 25 mm (MD, machine-direction width)×150 mm (CD, cross-direction width), and the size of the clamps at both ends of the specimen in the cross-direction is 25 mm, the portions of the specimen held by the clamps are not stretched, so the actual width of the specimen being stretched is 150−25×2=100 mm, which corresponds to the width of the large cut piece of 10 cm.

For the small cut piece, the size of the specimen is 25 mm (MD, machine-direction width)×100 mm (CD, cross-direction width), and the size of the clamps at both ends of the specimen in the cross-direction is 25 mm, the portions of the specimen held by the clamps are not stretched, so the actual width of the specimen being stretched is 100−25×2=50 mm, which corresponds to the width of the small cut piece of 5 cm.

The tensile test method is to: stretch the material from its natural state (the start of the curves in FIGS. 9 to 13, in which tensile force=0, elongation=0%) to its tensile limit, that is, until both the elastic material and the elastic non-woven fabrics are broken (the end of the curves in FIGS. 9 to 13). The stretching speed is 500 mm/min. The test results are based on the average of at least 5 specimens.

The tensile force used during the stretching process (that is, the tensile force subjected by the material) and the corresponding elongation are plotted as stress-strain graphs in FIGS. 9 to 13, and the elongation and tensile force (recovery force) of each material corresponding to the end of the curves (that is, tensile limit) are recorded in columns 8 to 9 of Table 1.

TABLE 1

| Unit | Elastic material Elongation — | (Elastic) non-woven fabric Elongation — | (Elastic) non-woven fabric Shrinkage — | ½ Fin space mm | Tooth space mm | (Elastic) non-woven fabric Cutting width cm | (Elastic) non-woven fabric Elongation — | (Elastic) non-woven fabric Recovery force g/in |
|---|---|---|---|---|---|---|---|---|
| EX1 | 980% | 200% | 56.5% | 1.6 | 4 | 10 | 461% | 5506 |
| EX2 | 980% | 200% | 67.7% | 3.5 | 4 | 10 | 657% | 5518 |
| EX3 | 980% | 200% | 69.7% | 1.6 | 2.5 | 10 | 635% | 5503 |
| EX4 | 980% | 200% | 79.2% | 3.5 | 2.5 | 10 | 946% | 5509 |
| EX5 | 980% | 200% | 69.7% | 1.6 | 2.5 | 5 | 317% | 5513 |
| EX6 | 980% | 200% | 79.2% | 3.5 | 2.5 | 5 | 473% | 5511 |
| CE1 | 980% | — | — | — | — | 10 | 337% | 4682 |
| CE2 | 980% | — | — | — | — | 10 | 234% | 2835 |

As can be seen from the results in Table 1, in Examples 1 to 6 of the present invention, at the time that the elastic composite non-woven fabrics reach the tensile limit, the elongation is about 300 to 1000%, and the recovery force (tensile force) is greater than 5500 g/in among all of them.

For Comparative Example 1, due to the limitations of the production efficiency of the stretching clamp, the stretching ratio of the elastic material, and the non-stretchable property of the ordinary non-woven fabrics, the tensile property of such composite non-woven fabric is moderate, at the time that the composite non-woven fabric reaches the tensile limit, the elongation can only reach 250 to 350%, and the recovery force is less than 5000 g/in.

For Comparative Example 2, because the non-woven fabric tissue, which has tensile properties before, is damaged, the recovery force of such composite non-woven fabric is provided by the elastic material only, and its tensile property is not usually high, at the time that the composite non-woven fabric reaches the tensile limit, the elongation is less than 250%, and the recovery force is less than 3000 g/in.

From the above results, it can be seen that the elongation and recovery force of the elastic composite non-woven fabric of the present invention (Examples 1 to 6) when reaching the tensile limit are significantly better than those of the composite non-woven fabrics of the prior art (Comparative Examples 1 to 2).

Figure 12:
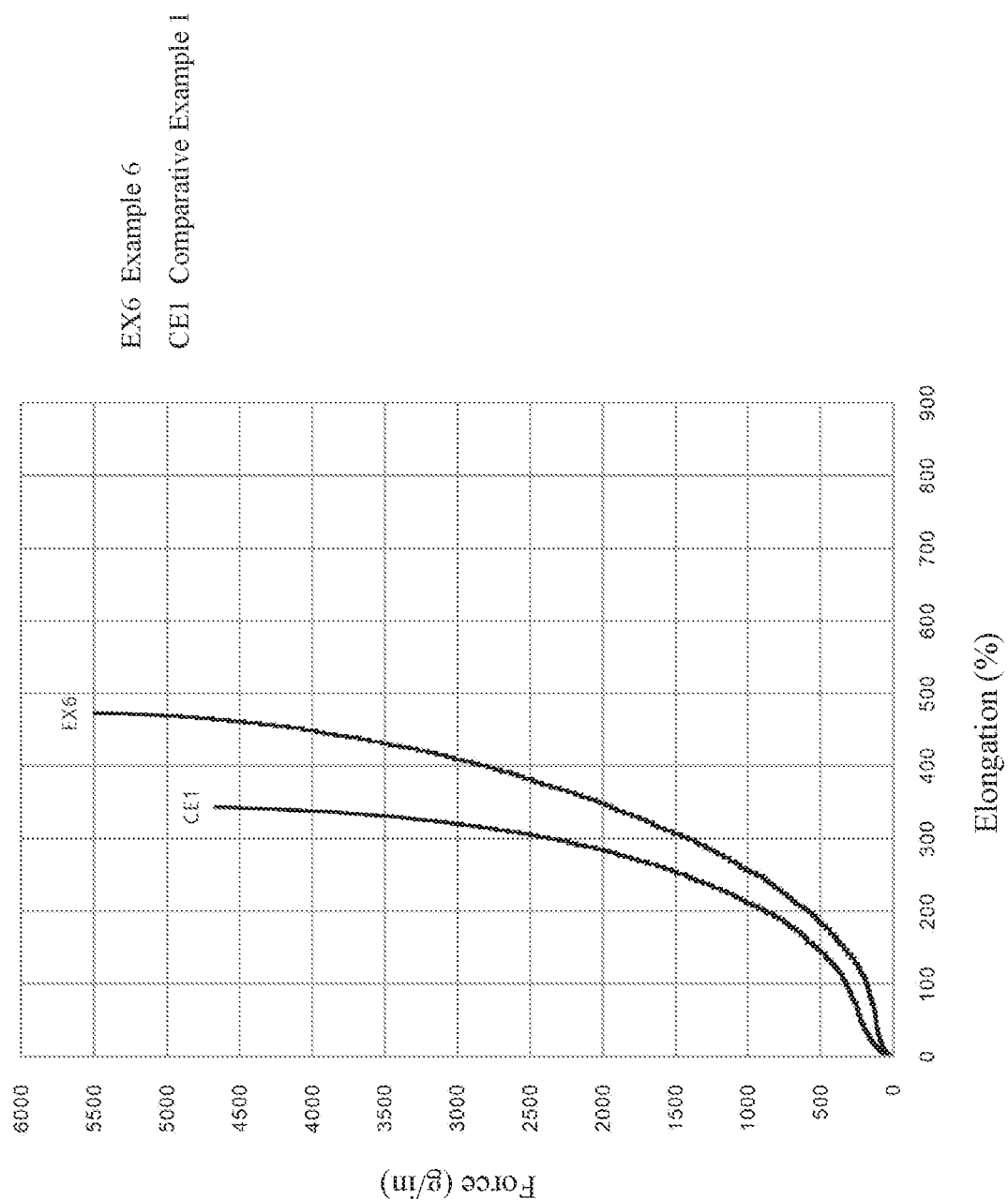
FIG. 12 illustrates the results of tensile test for the elastic composite non-woven fabrics according to Examples 6 and Comparative Example 1 of the present invention.
Figure 13:
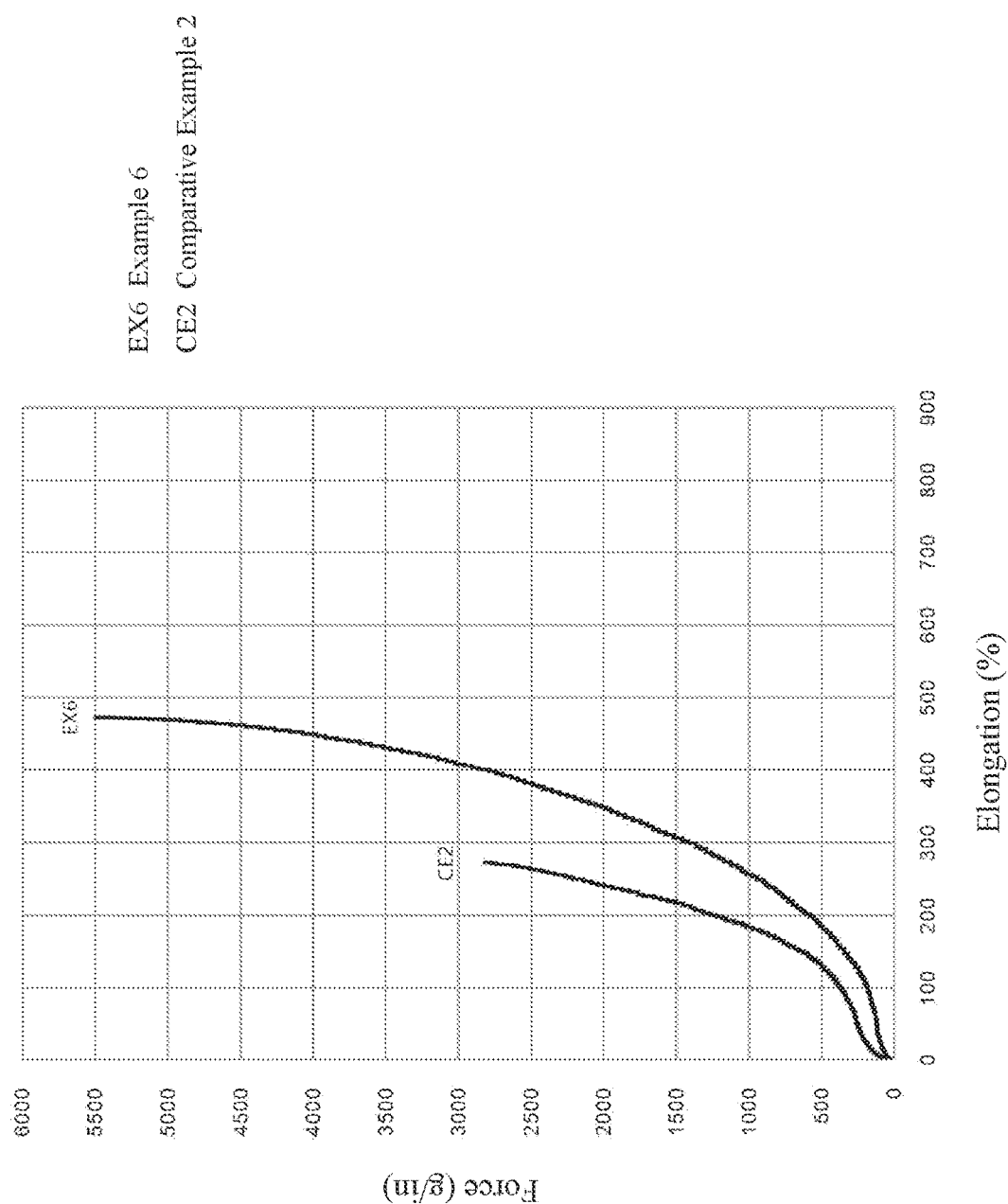
FIG. 13 illustrates the results of tensile test for the elastic composite non-woven fabrics according to Examples 6 and Comparative Example 2 of the present invention.

In particular, referring to the results of FIG. 12, it can be seen from the comparison results of Example 6 and Comparative Example 1 that Example 6 requires only half the cutting width relative to Comparative Example 1 to achieve an elongation that is comparable to (or even superior to) that of Comparative Example 1 when reaching the ultimate stretched width, it shows that the elastic composite non-woven fabric of the present invention requires only about half the cutting width relative to the composite non-woven fabric of the prior art to achieve similar or even superior performance. In addition, the same conclusion as described above was obtained by the comparison results of Example 6 and Comparative Example 2 with reference to the results of FIG. 13.

In summary, the present invention is effective in that, for example, by means of the manufacturing equipment or manufacturing method of the elastic composite non-woven fabric, two pieces of elastic non-woven fabrics are pre-shrunk to form a wavy surface first, and then the two pieces of pre-shrunk elastic non-woven fabrics are bonded to the upper surface and the lower surface of the elastic material. Therefore, the elastic composite non-woven fabric of the present invention can have high elongation, high tensile strength and high recovery force, so that the surface of the elastic composite non-woven fabric forms a certain degree of regular wavy folds.

In addition, because the elongation of the elastic composite non-woven fabric is greatly improved, the user can use a smaller cutting width. Therefore, in the factory, it is possible to divide each cylindrical master-roll of the elastic composite non-woven fabric into more cylindrical sub-rolls of the elastic composite non-woven fabric, thereby improving the production efficiency. Moreover, the elastic composite non-woven fabric of the present invention can meet the requirements of higher stretchability and recovery force with smaller cutting width, which can greatly improve the comfort and wrapping performance.

In practical application, for the elastic composite non-woven fabric of the present invention, only ½ to ⅓ of the cutting width relative to that of the existing elastic composite non-woven fabric is required to meet the requirements of stretchability and recovery force. As a result, the material used for the end products can be relatively reduced, thereby reducing the use of packaging materials and reducing the volume of the product to maximize transportation efficiency (especially in bandage applications).

Moreover, due to the upper and lower fins of the adjustable device, the shrinking degree of the elastic non-woven fabrics can be adjusted according to the product requirements, so as to achieve the best balance between the stretchability and recovery force of the elastic composite non-woven fabric, which can greatly improve the comfort and wrapping performance of the wearable application.

Those mentioned above are only preferred embodiments for explaining the present invention, but not intend to limit the present invention in any forms, so that any modifications or verification relating to the present invention made in the same spirit of the invention should still be included in the scope of the invention as intended to be claimed.

What is claimed is:
1. A manufacturing equipment for an elastic composite non-woven fabric, comprising:

an upper part, which is provided with an upper feed roller, an upper shrink roller, an upper bonding roller, and a plurality of upper fins;
a middle part, which is provided with a middle feed roller and a winding roller; and
a lower part, which is provided with a lower feed roller, a lower shrink roller, a lower bonding roller, and a plurality of lower fins, wherein
the upper shrink roller and the lower shrink roller each includes:
  a body, which is in a column shape;
  a first thread and a second thread, which are disposed on the body of corresponding one of the upper shrink roller and the lower shrink roller, and arranged symmetrically with respect to a mid-perpendicular plane of a longitudinal axis of the corresponding one of the upper shrink roller and the lower shrink roller; and
the upper bonding roller and the lower bonding roller each includes:
  a main body, which is in a column shape;
  a plurality of teeth, which are provided, in parallel to each other at a fixed interval, on an outer peripheral surface of the main body of corresponding one of the upper bonding roller and the lower bonding roller, and perpendicular to a longitudinal axis of the corresponding one of the upper bonding roller and the lower bonding roller; and
  a plurality of grooves, which are formed in a portion of the corresponding one of the upper bonding roller and the lower bonding roller where the teeth are not disposed; and
the upper fins and the lower fins are each in a flat shape and each includes:
  a first end pivotally fixed to the manufacturing equipment for the elastic composite non-woven fabric;
  a second end disposed in a corresponding one of the grooves; and
  a shoulder disposed between the first end and the second end;
  wherein a contour of each of the upper fins and the lower fins from the shoulder to the second end substantially matches a contour of the outer peripheral surface of the main body of corresponding one of the upper bonding roller and the lower bonding roller; and wherein
the upper feed roller, the middle feed roller, and the lower feed roller respectively feed a first elastic non-woven fabric, an elastic material, and a second elastic non-woven fabric,
the upper shrink roller receives the first elastic non-woven fabric, and the first thread and the second thread of the upper shrink roller are symmetrically arranged such that the first elastic non-woven fabric shrinks toward a center thereof along a direction parallel to the upper shrink roller, thereby the first elastic non-woven fabric enters gaps among the upper fins and the grooves and the teeth of the upper bonding roller in a non-stretched state, so that the first elastic non-woven fabric is wavy inwardly arranged and formed with regular wavy folds,
the lower shrink roller receives the second elastic non-woven fabric, and the first thread and the second thread of the lower shrink roller are symmetrically arranged such that the second elastic non-woven fabric shrinks toward a center thereof along a direction parallel to the lower shrink roller, thereby the second elastic non-woven fabric enters gaps among the lower fins and the grooves and the teeth of the lower bonding roller in a non-stretched state, so that the second elastic non-woven fabric is wavy inwardly arranged and formed with regular wavy folds, wherein a rotational speed of the upper feed roller, the upper shrink roller, the lower feed roller and the lower shrink roller is greater than that of the upper bonding roller and the lower bonding roller, thereby resulting a speed difference, and the first elastic non-woven fabric and the second elastic non-woven fabric are introduced between the upper fins and the lower fins due to the speed difference;

the teeth of the upper bonding roller and the teeth of the lower bonding roller are aligned and adjacently disposed, respectively, such that the first elastic non-woven fabric pre-shrunk and formed with the regular wavy folds, the elastic material fed by the middle feed roller, and the second elastic non-woven fabric pre-shrunk and formed with the regular wavy folds are bonded together at a portion where the teeth of the upper bonding roller and the teeth of the lower bonding roller are contacted, thereby forming an elastic composite non-woven fabric, and the winding roller winds the elastic composite non-woven fabric for collection.

2. The manufacturing equipment for the elastic composite non-woven fabric according to claim 1, wherein the upper fins and the lower fins are metal fins.

3. The manufacturing equipment for the elastic composite non-woven fabric according to claim 1, wherein a space between adjacent teeth of the upper bonding roller and a space between adjacent teeth of the lower bonding roller are adjustable, and/or a space between corresponding upper fin and lower fin is adjustable.

4. The manufacturing equipment for the elastic composite non-woven fabric according to claim 1, wherein relative to the middle part, the upper feed roller, the upper shrink roller, the upper bonding roller, and the upper fins are arranged symmetrically with the lower feed roller, the lower shrink roller, the lower bonding roller, and the lower fins, respectively.

5. The manufacturing equipment for the elastic composite non-woven fabric according to claim 1, wherein the upper feed roller, the upper shrink roller, the upper bonding roller, the middle feed roller, the winding roller, the lower feed roller, the lower shrink roller, and the lower bonding roller are arranged in parallel to each other.

* * * * *